United States Patent
Park et al.

(10) Patent No.: US 7,308,306 B1
(45) Date of Patent: *Dec. 11, 2007

(54) SYSTEM AND METHOD FOR DYNAMIC VENTRICULAR OVERDRIVE PACING

(75) Inventors: Euljoon Park, Valencia, CA (US); Peter Boileau, Valencia, CA (US); Joseph J. Florio, Bend, OR (US); Gene A. Bornzin, Simi Valley, CA (US); Eric Falkenberg, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 566 days.

This patent is subject to a terminal disclaimer.

(21) Appl. No.: 10/456,060

(22) Filed: Jun. 6, 2003

Related U.S. Application Data

(63) Continuation-in-part of application No. 10/036,026, filed on Dec. 21, 2001, now Pat. No. 6,804,556, which is a continuation of application No. 09/471,788, filed on Dec. 23, 1999, now Pat. No. 6,519,493.

(51) Int. Cl.
*A61N 1/368* (2006.01)
(52) U.S. Cl. .......................................... 607/9
(58) Field of Classification Search ............... 600/373, 600/374, 509, 515, 516, 518, 519, 521; 607/4, 607/5, 7, 9, 11, 14, 25, 28, 116, 119, 127, 607/130
See application file for complete search history.

(56) References Cited

U.S. PATENT DOCUMENTS

| | | | |
|---|---|---|---|
| 4,052,991 A | 10/1977 | Zacouto | 128/419 PG |
| 4,503,857 A | 3/1985 | Boute et al. | 128/419 PG |

(Continued)

FOREIGN PATENT DOCUMENTS

EP 0904802 A2 8/1998

(Continued)

OTHER PUBLICATIONS

Weintraub, Rogert G., MB, BS, FRACP, et al., "The Congenital Long QT Syndromes in Childhood", JACC, pp. 674-680, vol. 16, No. 3 (Sep. 1990).

(Continued)

*Primary Examiner*—Kristen D. Mullen
*Assistant Examiner*—Frances P. Oropeza

(57) ABSTRACT

Techniques are provided for overdrive pacing the ventricles using a pacemaker wherein an increase in an overdrive pacing rate is performed primarily to achieve a high degree of rate smoothing. The ventricles are paced at an overdrive pacing rate selected to permit the detection of the least some intrinsic ventricular pulses and then the overdrive pacing rate is dynamically adjusted based on the detected intrinsic ventricular pulses. In one example, an increase in the ventricular overdrive rate is performed only in response to detection of at least two intrinsic ventricular beats within a predetermined search period. If at least two intrinsic ventricular beats are not detected within the search period, the overdrive pacing rate is decreased. Various techniques are also provided for determining when to activate ventricular overdrive pacing depending, in part, on the capabilities of the particular pacemaker, the current mode of operation, the density of premature ventricular contractions, the degree of heart rate stability, and the presence of atrial fibrillation. Adaptive techniques for automatically adjusting ventricular overdrive pacing control parameters are also described.

22 Claims, 17 Drawing Sheets

U.S. PATENT DOCUMENTS

| | | | |
|---|---|---|---|
| 4,940,052 A | 7/1990 | Mann et al. | 128/419 PG |
| 5,480,413 A * | 1/1996 | Greenhut et al. | 607/14 |
| 5,683,429 A | 11/1997 | Mehra | 602/14 |
| 5,951,593 A | 9/1999 | Lu et al. | 607/14 |
| 5,978,709 A | 11/1999 | Begemann et al. | 607/14 |
| 6,058,328 A * | 5/2000 | Levine et al. | 607/14 |
| 6,078,836 A | 6/2000 | Bouhour et al. | 607/14 |
| 6,141,586 A | 10/2000 | Mower | 607/9 |
| 6,161,041 A | 12/2000 | Stoop et al. | 607/14 |
| 6,185,459 B1 | 2/2001 | Mehra et al. | 607/14 |
| 6,285,907 B1 | 9/2001 | Kramer et al. | 607/9 |

FOREIGN PATENT DOCUMENTS

| | | |
|---|---|---|
| EP | 0965361 A2 | 5/1999 |
| WO | WO 99/61101 | 12/1999 |

OTHER PUBLICATIONS

Langendorf, R., MD, et al., "Mechanisms of Intermittent Ventricular Bigeminy", Circulation, pp. 422-430, vol. X1 (Mar. 1955).

Moss, Arthur J., MD, et al., "Efficacy of Permanent Pacing in the Management of High-Risk Patients with Long QT Syndrome", Circulation, pp. 1524-1529, vol. 84, No. 4 (Oct. 1991).

Ohe, Tohru, MD, et al., "The Effects of Cycle Length on the Fragmented Atrial Activity Zone in Patients with Sick Sinus Syndrome", J. Electrocardiology, pp. 364-368, 20(5) (1987).

Levine, P.A., et al., "Device Management of Paroxysmal Atrial Fibrillation Using the Dynamic Atrial Overdrive Algorithm", pp. 86-95, Herz-Schrittmacher, 20 (2000).

Fontaine, G., et al., "Value and Limitaitons of the DPG-1 Pacemaker Anti-Arrhythmic Functions", Steinkopff Verlag Pub. Darmstadt (1985) pp. 224-237.

Ragonese, Pietro, et al., "Permanent Overdrive Atrial Pacing in the Chronic Management of Recurrent Postoperative Atrial Reentrant Tachycardia in Patients with Complex Congenital Heart Disease", PACE, pp. 2917-2923, vol. 20, Part I (Dec. 1997).

Coumel, Phillippe, et al., "Long-Term Prevention of Vagal Atrial Arrhythmias by Atrial Pacing at 90/Minute: Experience with 6 Cases", PACE, pp. 552-560, vol. 6, Part I (May-Jun. 1983).

Murgatroyd, Francis D., et al., A New Pacing Algorithm for Overdrive Suppression of Atrial Fibrillation:, PACE, vol. 17, Part II, pp. 1966-1973 (Nov. 1994).

Coumel, Philippe et al., "Long-Term Prevention of Vagal Atrial Arrhythmias by Atrial Pacing at 90/Minute: Experience with 6 Cases," PACE,vol. 6 (May-Jun. 1983), pp. 552-560.

Levine, P.A. et al., "Device Management of Paroxysmal Atrial Fibrillation Using the Dynamic Atrial Overdrive Algorithm," Herz-Schrittmacher, 20, Nr. 1 (2000), pp. 86-95.

Ohe, Tohru MD, et al., "The Effects of Cycle Length on the Fragmented Atrial Activity Zone in Patients with Sick Sinus Syndrome," J. Electrocardiology 20(5), pp. 364-368.

Ragonese, Pietro et al., "Permanent Overdrive Atrial Pacing in the Chronic Management of Recurrent Postoperative Atrial Reentrant Tachycardia in Patients with Complex Congenital Heart Disease," PACE 1997; 20 (Pt. 1): 2917-2923.

Weintraub, Robert G. MB, BS, FRACP et al., "The Congenital Long QT Syndromes in Childhood," JACC, vol. 16, No. 3 (Sep. 1990), pp. 674-680.

* cited by examiner

SYSTEM AND METHOD FOR DYNAMIC VENTRICULAR OVERDRIVE PACING

RELATED APPLICATIONS

This patent application is a Continuation-in-Part (CIP) of U.S. patent application Ser. No. 10/036,026, filed Dec. 21, 2001, now U.S. Pat. No. 6,804,556, entitled "Methods And Apparatus For Overdrive Pacing Heart Tissue Using An Implantable Cardiac Stimulation Device", of Florio et al., which was a Continuation of U.S. patent application Ser. No. 09/471,788, filed Dec. 23, 1999, now U.S. Pat. No. 6,519,493.

FIELD OF THE INVENTION

The invention generally relates to implantable cardiac stimulation devices such as pacemakers, and in particular, to techniques for overdrive pacing heart tissue to prevent or terminate dysrhythmias.

BACKGROUND OF THE INVENTION

A dysrhythmia is an abnormal heart beat pattern. One example of dysrhythmia is bradycardia wherein the heart beats at an abnormally slow rate or wherein significant pauses occur between consecutive beats. Other examples of dysrhythmias include tachyarrhythmias wherein the heart beats at an abnormally fast rate. With atrial tachycardia, such as atrial fibrillation (AF), the atria of the heart beat abnormally fast. With ventricular tachycardia, the ventricles of the heart beat abnormally fast. Though often unpleasant for the patient, a tachycardia is typically not fatal. However, some tachycardias, particularly ventricular tachycardia, can trigger ventricular fibrillation wherein the heart beats chaotically such that there is little or no net flow of blood from the heart to the brain and other organs. Ventricular tachycardia, if not terminated, is fatal. Hence, it is highly desirable to prevent or terminate dysrhythmias, particularly ventricular tachycardias.

One technique for preventing or terminating dysrhythmias is to overdrive pace the heart wherein a implantable cardiac stimulation device, such as a pacemaker or implantable cardioverter defibrillator (ICD), applies electrical pacing pulses to the heart at a rate somewhat faster than the intrinsic heart rate of the patient. For bradycardia, the cardiac stimulation device may be programmed to artificially pace the heart at a rate of 60 to 80 pulses per minute (ppm) to thereby prevent the heart from beating too slow and to eliminate any long pauses between heart beats. To prevent tachyarrhythmias from occurring, the cardiac stimulation device artificially paces the heart at a rate of at least five to ten beats per minute faster than the intrinsic tachyarrhythmia heart rate of the patient. In other words, a slight artificial tachycardia is induced and maintained in an effort to prevent an actual tachycardia from arising. If an actual tachycardia occurs, such as a supraventricular tachycardia (SVT) wherein the heart may begin beating suddenly at 150 beats per minute (bpm) or more, the cardiac stimulation device senses tachycardia and immediately begins pacing at a rate of at least five to ten ppm faster than the tachycardia, then slowly decreases the pacing rate in an effort to slowly reduce the heart rate back to a normal resting rate thereby terminating the tachycardia.

It is believed that overdrive pacing is effective for at least some patients for preventing or terminating the onset of an actual tachycardia for the following reasons. A normal, healthy heart beats only in response to electrical pulses generated from a portion of the heart referred to as the sinus node. The sinus node pulses are conducted to the various atria and ventricles of the heart via certain, normal conduction pathways. In some patients, however, additional portions of the heart also generate electrical pulses referred to as "ectopic" pulses. Each pulse, whether a sinus node pulse or an ectopic pulse has a refractory period subsequent thereto during which time the heart tissue is not responsive to any electrical pulses. A combination of sinus pulses and ectopic pulses can result in a dispersion of the refractory periods which, in turn, can trigger a tachycardia. By overdrive pacing the heart at a uniform rate, the likelihood of the occurrence of ectopic pulses is reduced and the refractory periods within the heart tissue are rendered uniform and periodic. Thus, the dispersion of refractory periods is reduced and tachycardias triggered thereby are substantially avoided. If a tachycardia nevertheless occurs, overdrive pacing at a rate faster than a tachycardia helps to eliminate ectopic pulses and reduce refractory period dispersion, and thereby helps to terminate the tachycardia.

Thus, it is desirable within patients prone to tachyarrhythmias to ensure that most beats of the heart are paced beats, as any unpaced beats may be ectopic beats. A high percentage of paced beats can be achieved simply by establishing a high overdrive pacing rate. However, a high overdrive pacing rate has disadvantages as well. For example, a high overdrive pacing rate may be unpleasant to the patient, particularly if the artificially-induced heart rate is relatively high in comparison with the heart rate that would otherwise normally occur. A high heart rate may also cause possible damage to the heart or may possibly trigger more serious dysrhythmias, such as a ventricular fibrillation.

A high overdrive rate may be especially problematic in patients suffering from heart failure, particularly if the heart failure is due to an impaired diastolic function. A high overdrive rate may actually exacerbate heart failure in these patients. Also, a high overdrive rate may be a problem in patients with coronary artery disease because increasing the heart rate decreases diastolic time and decreases perfusion, thus intensifying ischemia. Also, the need to apply overdrive pacing pulses operates to deplete a power supply of the implantable cardiac stimulation device, perhaps requiring frequent surgical replacement of the power supply.

Problems associated with overdrive pacing are particular severe for certain aggressive overdrive techniques which trigger an increase in the pacing rate based upon detection of a single intrinsic heart beat. With such techniques, a significant increase in the pacing rate is triggered by detection of a single intrinsic heart beat so as to respond promptly to the occurrence of a high rate tachycardia, such as an SVT. As a result, even in circumstances where a high rate tachycardia has not occurred, the detection of a single intrinsic heart beat can cause a significant increase in the overdrive rate, which may be reduced only gradually. If a second intrinsic heart beat is detected before the overdrive rate has been gradually lowered to a standard overdrive pacing rate, a still further increase in the pacing rate occurs. As can be appreciated, the foregoing can cause the overdrive pacing rate to increase significantly, perhaps to 150 ppm or more, even though no high rate tachycardia has occurred.

Hence, it would be desirable to provide techniques for overdrive pacing which reduce the average overdrive pacing rate, yet still attain a sufficiently high rate to significantly reduce the likelihood of a dysrhythmia within the patient or to terminate a dysrhythmia if one nevertheless occurs. In particular, it would be highly desirable to provide overdrive pacing techniques which permit a certain percentage of paced beats (such as 90% or 95%) to be sustained by the cardiac stimulation device so as to enable the overdrive rate to be minimized while still ensuring that most beats of the heart are paced beats. It was to these ends that aspects of the invention of the parent application were primarily directed.

The parent patent application referenced above was primarily directed to a technique for overdrive pacing the atria wherein an increase in the overdrive pacing rate is performed only in response to detection of at least two intrinsic atrial beats within a predetermined search period. In one specific technique, an increase in the atrial pacing rate occurs only if two P-waves are detected within X cardiac cycles of one another. In another specific technique, the overdrive rate is increased only if at least two P-waves are detected within a block of N consecutive cardiac cycles. In both techniques, the overdrive rate is decreased if no increase has occurred in the last Z cardiac cycles. By increasing the overdrive pacing rate only in response to detection of at least two P-waves within a predetermined number of cardiac cycles, an excessively high overdrive pacing rate is avoided which might otherwise occur if a rate increase were triggered based upon detection only of a single P-wave.

Insofar as the ventricles are concerned, overdrive pacing is also beneficial. However, unlike the atria, where it is generally desirable to achieve a high percentage of overdrive paced beats, with the ventricles it is generally best to provide rate smoothing, i.e. to provide a generally uniform ventricular rate as a function of time. Significant variations in the ventricular rate as a function of time presents a considerable annoyance to the patient who feels his or her heart rate increasing or decreasing frequently. Moreover, significant variations in ventricular rate can sometimes trigger atrial and ventricular tachyarrhythmias.

Various techniques have been developed in an attempt to provide rate smoothing of the ventricular rate. However, heretofore, ventricular rate smoothing techniques have often attempted to achieve rate smoothing primarily through fixed, non-overdrive ventricular pacing. In this regard, it has been found that there is a correlation between the degree of variation in the actual ventricular rate and the fixed rate at which the ventricles are paced. If the ventricles are paced at, for example, a fixed rate of 80 ppm, the resulting ventricular rate varies between the fixed rate of 80 ppm and much higher rates, such as 140 ppm. However, by pacing the ventricles at a higher fixed rate, for example, 100 ppm, the actual ventricular rate may only vary between the fixed rate of 100 ppm and a reduced upper rate of, perhaps, only 130 ppm. By pacing the ventricles at a still higher fixed rate, for example, 120 ppm, the actual ventricular rate may vary only within a much narrower range, such as from 120 to 125 ppm. In other words, the higher the fixed ventricular paced rate, the smoother the resulting ventricular rate.

Thus, rate smoothing of the ventricles can be achieved by pacing the ventricles at a high fixed rate. However, fixed rate pacing of the ventricles can result in "pacemaker syndrome", which is typically characterized by hypotension, shortness of breath, and fatigue. Also, in many cases, fixed rate pacing of the ventricles at a high rate can cause "concealed retrograde conduction", wherein a retrograde impulse travels from the ventricular pacing site back to the AV junction. Although this may not cause the atria to fire, the result is a lengthening of the AV junctional repolarization time, possibly adversely affecting the proper function of the atria and triggering atrial tachycardias.

Certain other ventricular rate smoothing techniques seek to achieve smoothing using adjustable ventricular pacing rates. However, these techniques appear to suffer from problems similar to those described above in connection with conventional atrial overdrive techniques, namely such techniques may be too sensitive to changes in the intrinsic ventricular rate. As an example of a technique which seeks to achieve ventricular rate smoothing using adjustable ventricular pacing rates see U.S. Pat. No. 5,792,193 to Stoop, entitled "Pacemaker System And A Method With Ventricular Rate Smoothing During High Rate Atrial Arrhythmia." In the technique described by Stoop, during a pathologically high atrial rate episode, the pacemaker determines a ventricular pacing escape interval, corresponding to a flywheel rate, with the flywheel rate set at the beginning of the episode to be substantially equal to the atrial rate just before the high rate episode. As long as the episode continues, the flywheel rate is incremented upward whenever a ventricular sense occurs, thereby attempting to follow the average ventricular rate. Whenever a flywheel escape interval times out and a ventricular pacing pulse is delivered, flywheel rate is decremented. Ventricular sensing and pacing occurs only after timeout of the flywheel escape interval. Thus, detection of a single ventricular intrinsic sensed event causes an increase in the flywheel rate; whereas failure to detect an intrinsic ventricular event during the flywheel escape interval triggers an immediate decrease in the flywheel rate. As such, the pacemaker may be too sensitive to individual ventricular intrinsic sensed beats to provide for optimal ventricular rate smoothing. Moreover, the technique of Stoop only appears to provide for rate smoothing during episodes of pathologically high atrial rates and does not provide rate smoothing at other times.

In any case, it does not appear that, heretofore, any techniques have been developed for performing ventricular overdrive pacing, either for the purpose of achieving ventricular rate smoothing or for other reasons, which effectively controls and limits changes in the ventricular overdrive rate. Hence, it would be desirable to provide techniques for providing dynamic overdrive pacing of the ventricles either for ventricular rate smoothing or for other reasons, and aspects of the present CIP application are primarily directed to that end. Whereas atrial overdrive pacing is typically performed more or less continuously once activated by a physician, with ventricular overdrive pacing, care should be taken to ensure that the overdrive pacing of the ventricles is performed only when needed so as not to unduly increase the risk of ventricular dysrhythmias. Accordingly, techniques are also provided herein for activating and deactivating ventricular overdrive pacing based on various factors such as the capabilities of the particular pacing device (i.e. DDD vs. VVI pacers), the mode of operation (i.e. tracking vs. non-tracking mode) and the general medical condition of the patient (i.e. chronic AF vs. non-chronic AF.) In particular, techniques are provided for evaluating of the density of premature ventricular contractions (PVCs) and for disabling ventricular overdrive pacing in circumstances where overdrive pacing inadvertently triggers an increase in PVC density, which can in turn trigger ventricular tachyarrhythmia.

SUMMARY

In accordance with one illustrative embodiment, various techniques are provided for performing dynamic ventricular overdrive (DVO) pacing using an implantable cardiac stimulation device. In accordance with the general method, the ventricles are paced at an overdrive pacing rate selected to permit the detection of at least some intrinsic ventricular pulses and then the overdrive pacing rate is dynamically adjusted based on the intrinsic ventricular pulses, principally for the purposes of rate smoothing. Since the technique is a dynamic technique based on the detection of intrinsic ventricular pulses rather than a fixed-rate technique, the aforementioned problems associated with fixed rate ventricular pacing are substantially avoided.

In one example, an increase in the ventricular overdrive rate is performed only in response to detection of at least two intrinsic ventricular beats within a predetermined search period. Initially, a ventricular overdrive pacing rate is determined and the ventricles are paced at the overdrive pacing rate. Intrinsic ventricular beats arising during overdrive pacing are detected. If at least two intrinsic ventricular beats are detected within a first predetermined search period, then the overdrive pacing rate is increased by a predetermined rate increment. If at least two intrinsic ventricular beats are not detected within a second predetermined search period, the overdrive pacing rate is decreased by a predetermined rate of decrements. By adjusting the ventricular overdrive rate based on the detection of at least two intrinsic ventricular beats, significant variations in the ventricular pacing rate that might otherwise be triggered by detection of individual intrinsic ventricular beats are thereby avoided.

Also, in accordance with certain illustrative embodiments, various techniques are provided for determining when to activate ventricular overdrive pacing based, in part, on the capabilities of the implantable cardiac stimulation device. In one example, if the implantable device includes an AF detector, ventricular overdrive pacing is preferably activated only during AF. If the implantable device is capable of Automatic Mode Switching (AMS) between a tracking mode and a non-tracking mode, ventricular overdrive pacing is preferably activated only while the device is in the non-tracking mode (i.e. within a DDI or VVI mode). If implantable device is a VVI device provided with a heart rate stability detector, ventricular overdrive pacing is preferably performed only when the degree of instability in the heart rate of the patient, as determined by the heart rate stability detector, exceeds a predetermined heart rate stability threshold. Alternatively, if the VVI device includes a PVC density detector for evaluating the density of PVCs, ventricular overdrive pacing is preferably activated only if the density exceeds a predetermined PVC density threshold. However, if following activation of ventricular overdrive pacing, PVC density still exceeds the threshold, then ventricular overdrive pacing is preferably permanently disabled within the device, since ventricular overdrive pacing, in that situation, may be proarrhythmic. If the implantable device is a DDD device incorporating a PVC density detector, ventricular overdrive pacing is preferably activated only when the PVC density exceeds the predetermined PVC density threshold. In specific example, the device is automatically switched to a DDI mode during overdrive pacing. If the implantable device is only configured for VVI pacing, then a signal is input from an external programmer indicating whether the patient has chronic AF and, if so, ventricular overdrive pacing is performed at all times; otherwise ventricular overdrive pacing is not performed.

In accordance with a further aspect, adaptive methods are provided for automatically varying ventricular overdrive pacing control parameters so as to achieve a target degree of smoothing of the ventricular rate or a target percentage of ventricular overdrive paced beats. Ventricular overdrive pacing pulses are applied to the ventricles in accordance with programmed values specifying overdrive pacing characteristics. The actual degree of smoothness or percentage of paced beats resulting from the overdrive pacing pulses is determined. The programmed values are then varied based upon the degree of smoothness or the percentage of paced beats resulting from the overdrive pacing pulses in an attempt to achieve either the target degree of smoothness or the target percentage of ventricular paced beats.

System and apparatus embodiments are also provided. Other aspects, features, and advantages will be apparent from the detailed description which follows in the combination with the attached drawings.

BRIEF DESCRIPTION OF THE DRAWINGS

The above and further features, advantages and benefits will be apparent upon consideration of the present description taken in conjunction with the accompanying drawings, in which.

DESCRIPTION OF THE PREFERRED EMBODIMENTS

The following description is of the best mode presently contemplated. This description is not to be taken in a limiting sense but is made merely for the purpose of describing the general principles of the invention. The scope of the invention should be ascertained with reference to the issued claims. In the description that follows, like numerals or reference designators will be used to refer to like parts or elements throughout.

Overview of Implantable Stimulation Device

Figure 1:
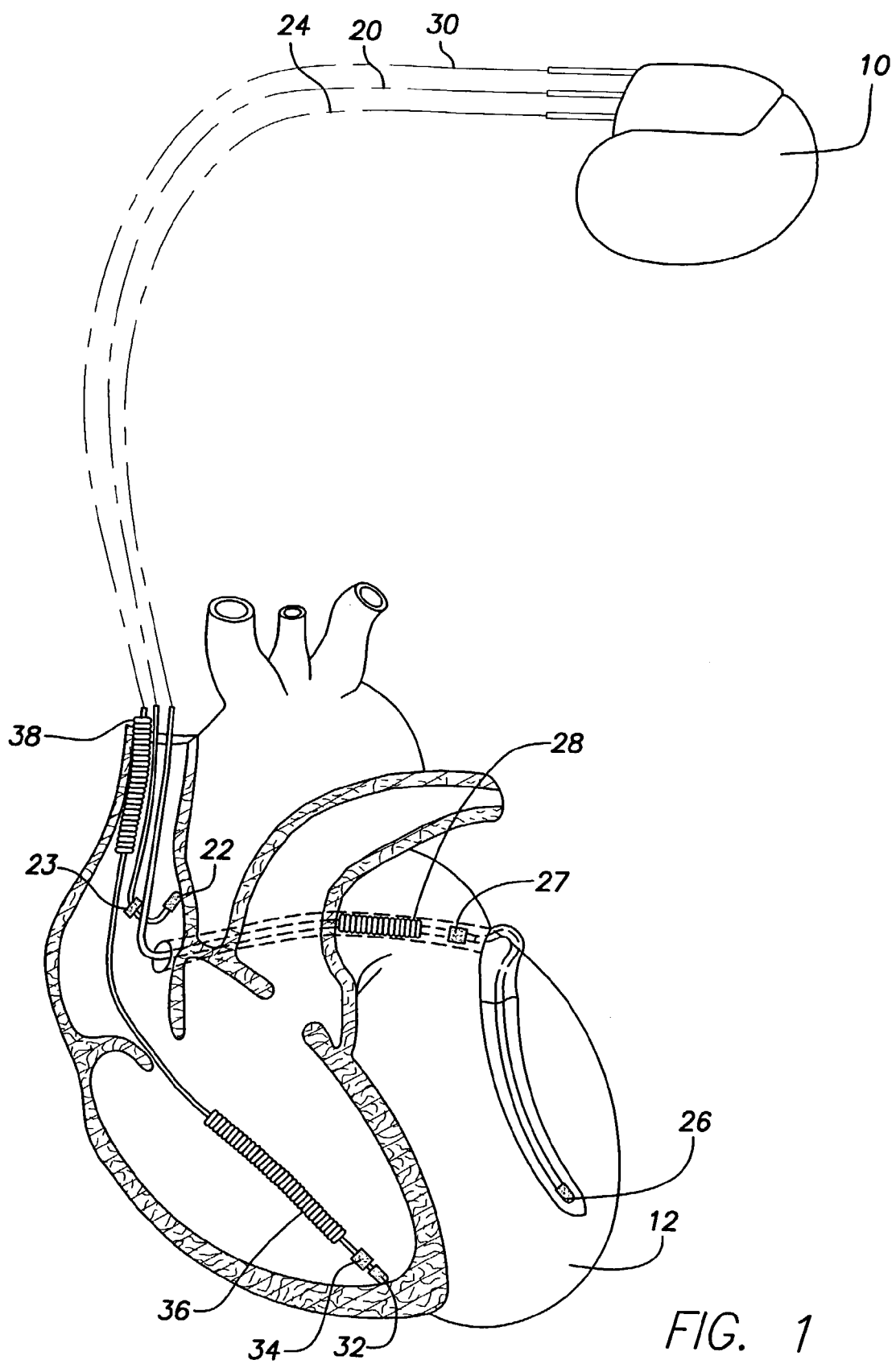
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which is typically implanted in the patient's right atrial appendage, and an atrial ring electrode 23.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
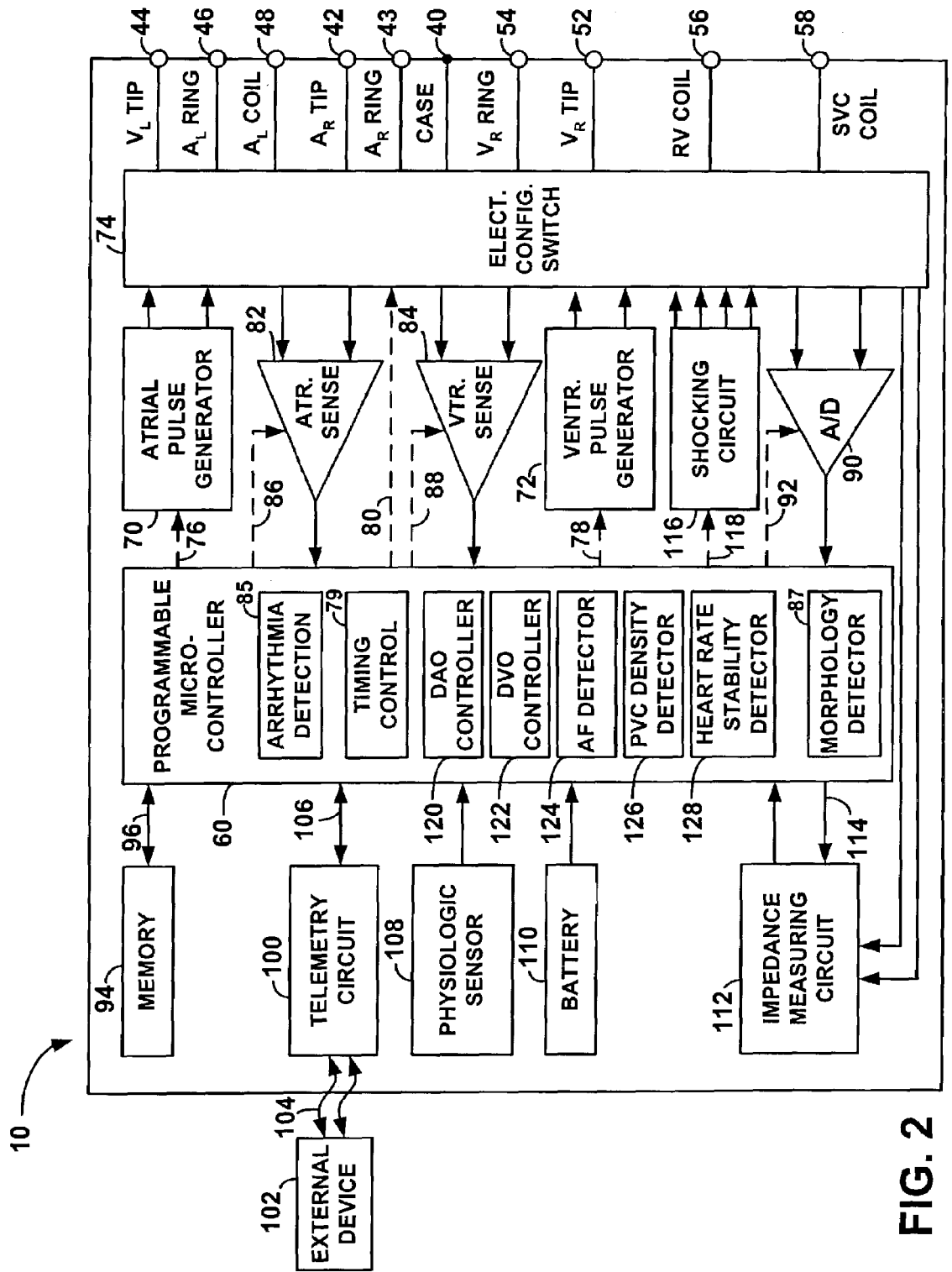
FIG. 2 is a functional block diagram of the multi-chamber implantable stimulation device of FIG. 1 illustrating the basic elements of a stimulation device which can provide cardioversion, defibrillation and pacing stimulation in four chambers of the heart and particularly illustrating DAO and DVO components.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. The connector also includes a right atrial ring terminal ($A_R$ RING) 43 adapted for connection to the atrial ring electrode 23.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes a timing control unit 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit under the control of microcontroller 60 via control lines 86 and 88 respectively, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Arrhythmia and morphology detection is performed under the control, respectively, of arrhythmia detection unit 85 and morphology detector 87 of the microcontroller.

Cardiac signals are also applied to the inputs of an analog-to-digital (A/D) data acquisition system 90. The data acquisition system 90, under the control of microcontroller 60 via control line 92 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In an exemplary embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The impedance measuring circuit 112 is not critical and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In addition, the stimulation device may be configured to perform AMS wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both chambers but only paces in the ventricle. A sensed event on the atrial channel triggers a ventricular output after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Additionally, the stimulation device includes both a DAO controller 120 for controlling atrial overdrive pacing and a DVO controller 122 for controlling ventricular overdrive pacing. DVO controller operates in cooperation with one more of an AF detector 124, a PVC density detector 126, and a heart rate stability detector 130. The operation of these components will be described below. Although both are show in a single stimulation device for the sake of completeness, in many cases only either the DAO controller or the DVO controller are provided.

Dynamic Atrial Overdrive Techniques

1. DAO Overview

Figure 3:
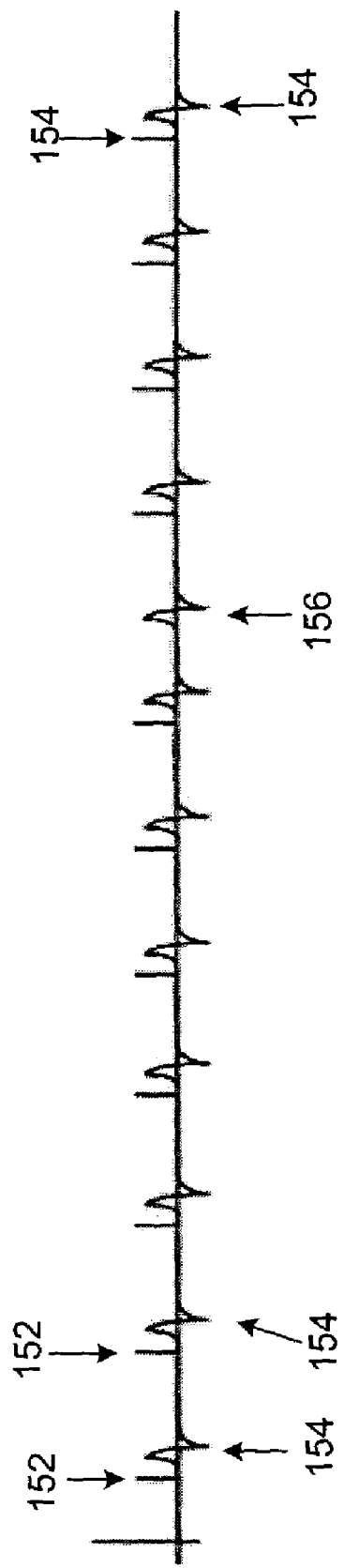
FIG. 3 is a timing diagram illustrating paced beats and un-paced beats within the heart of FIG. 1.

FIG. 3 illustrates a sequence of pacing pulses 152 administered by the DAO controller of the cardiac stimulation device of FIG. 2. Each electrical pacing pulse triggers an evoked response 154 representative of an artificially induced heart beat. Pulses 152 are administered at a constant pacing rate and, therefore, are separated by a constant pacing cycle length. FIG. 2 also illustrates a single un-paced beat 156 not preceded by a pacing pulse 152. Un-paced beat 154 may be, for example, an ectopic beat cause by a naturally occurring electrical signal generated within the heart from a location other than the sinus node from which normal sinus rhythm heart beats are naturally generated. As discussed above, ectopic beats have been found to sometimes trigger tachyarrhythmias and hence it is desirable to minimize the number of ectopic beats. Accordingly, the cardiac stimulation device of FIG. 1 performs an overdrive pacing algorithm intended to generate overdrive pacing pulses 152 at a sufficiently high rate to minimize the number of un-paced beats without causing an unnecessarily high heart rate. To this end, the cardiac stimulation device determines the actual degree of pacing resulting from the overdrive pacing pulses and adaptively modifies the overdrive pacing rate to maintain the actual degree of pacing at about a target degree of pacing wherein about 95% of the total beats are paced beats.

2. Exemplary DAO Techniques

Figure 4:
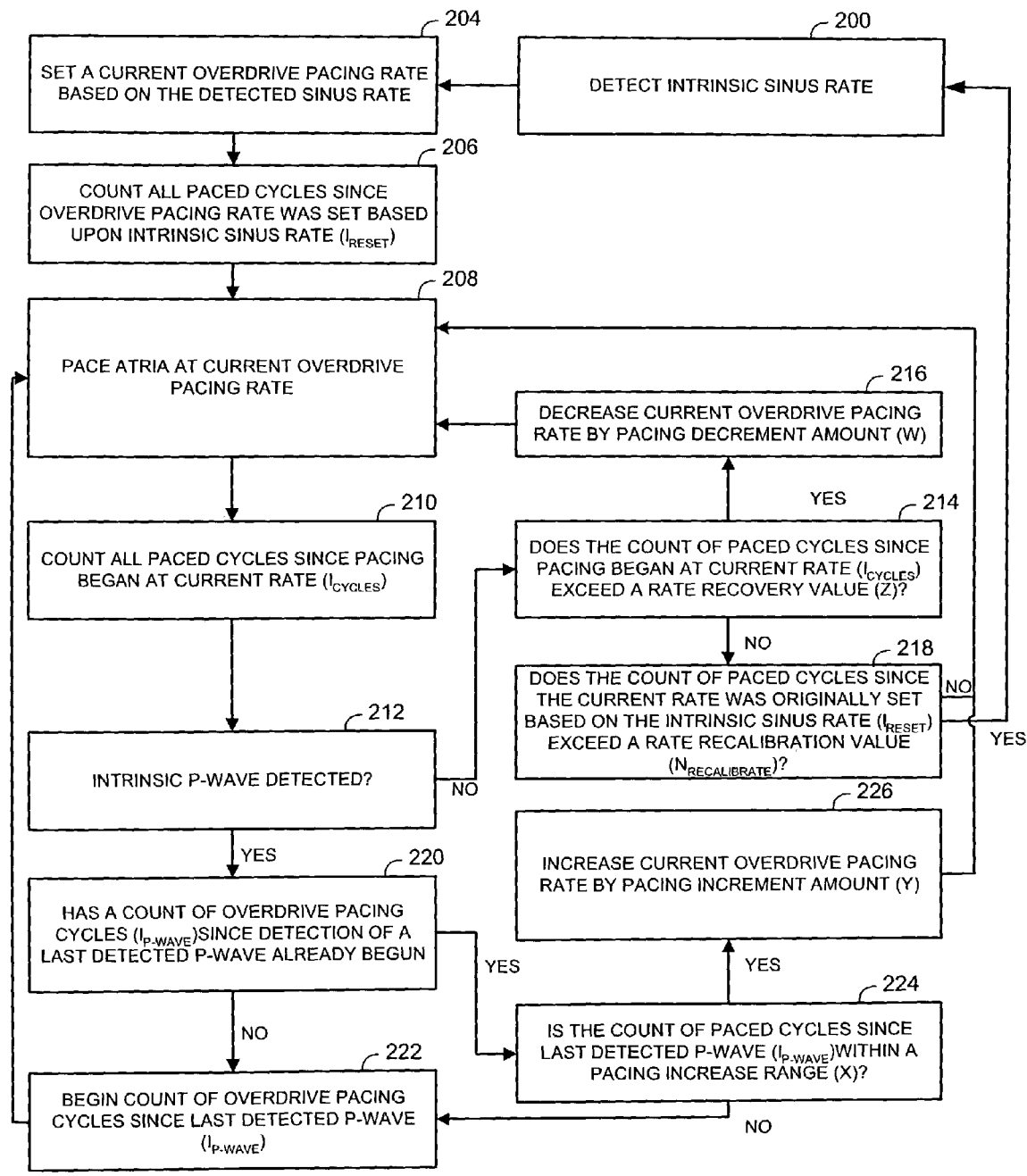
FIG. 4 is a flow chart illustrating a DAO pacing method wherein an overdrive pacing rate is increased only if at least two intrinsic events are detected within a predetermined number of cardiac cycles of one another.

FIG. 4 illustrates a technique for overdrive pacing a heart wherein an overdrive pacing rate is increased only in response to the detection of at least two intrinsic P-waves occurring within X cardiac cycles of one another wherein X is, typically, between eight and forty cardiac cycles.

Briefly, the technique is summarized as follows:
1. Identify P wave.
2. If another P-wave occurs within X cardiac cycles, increase pacing rate by Y bpm.
   a) X is programmable from about 8 to 40 cardiac cycles.
   b) Y is the programmable rate increase and is programmable to 5, 10,15, 20 or 25 ppm.
3. If Z cardiac cycles occur without a rate increase, then decrease rate by W ppm/cardiac cycle.
   a) Z is the dwell time before rate is decreased and is programmable from 8 to 40 cardiac cycles.
   b) W is programmable at 1, 2, 3, 4, or 5 ppm/cardiac cycle.

Additionally, the cardiac stimulation device periodically suspends pacing to permit detection of three consecutive P-waves. At that time, the sinus rate is computed based upon the detected P-waves and the overdrive pacing rate is reset to be equal to the sinus rate.

This technique will now be explained more fully with reference to FIG. 5. In these flow charts and any other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device.

Initially, at step 200, the intrinsic sinus rate is detected by detecting three consecutive P-waves. At step 204, a current overdrive pacing rate is set to be equal to the detected sinus rate. At step 206, the cardiac stimulation device begins to count the number of paced cycles ($I_{RESET}$) since the overdrive pacing rate was set based upon the intrinsic sinus rate. This count of paced cycles is eventually compared with a rate recalibration value in step 218 (described below) and if it exceeds the recalibration value, step 200 is repeated to detect a new intrinsic sinus rate for resetting of the overdrive pacing rate.

At step 208, the atria of the heart are paced at the current overdrive pacing rate. At step 210, the number of cycles ($I_{CYCLES}$) since pacing began at the current rate is counted. Note that, initially, $I_{RESET}$ and $I_{CYCLES}$ are equal to one another. However, as will be described, the values typically diverge from one another with further execution of the method steps. $I_{CYCLES}$ is eventually compared against a rate recovery value Z at step 214 (described below) and if $I_{CYCLES}$ exceeds Z, the overdrive pacing rate is decreased.

At step 212, the cardiac stimulation device detects any intrinsic P-waves. If no P-wave is detected, processing proceeds to step 214 wherein the count of paced cycles since pacing began at the current rate ($I_{CYCLES}$) is compared with the rate recovery value (Z). If $I_{CYCLES}$ exceeds Z, then step 216 is performed wherein the current overdrive pacing rate is decreased by a pacing decrement amount W preset to 1, 2, 3, 4, or 5 ppm per cardiac cycle. Processing then returns to step 208 for continued pacing at the newly reduced overdrive pacing rate. Thus, if at least $I_{CYCLES}$ of pacing occurs before detection of a single intrinsic P-wave, then the current overdrive pacing rate is reduced to provide for rate of recovery. If, at step 214, $I_{CYCLES}$ does not exceed Z, then step 218 is performed wherein the cardiac stimulation device determines whether the count of paced cycles since the current rate was originally set ($I_{RESET}$) exceeds a rate recalibration value ($N_{RECALIBRATION}$). If $I_{RESET}$ exceeds $N_{RECALIBRATION}$, then step 200 is again executed wherein a new sinus rate is detected and the overdrive pacing rate is reset to the new sinus rate. This ensures that the overdrive rate does not remain significantly different from the sinus rate for any extended period of time. If, at step 218, $I_{RESET}$ does not exceed $N_{RECALIBRATION}$, then processing returns to step 208 for additional pacing at the current overdrive pacing rate.

Figure 5:
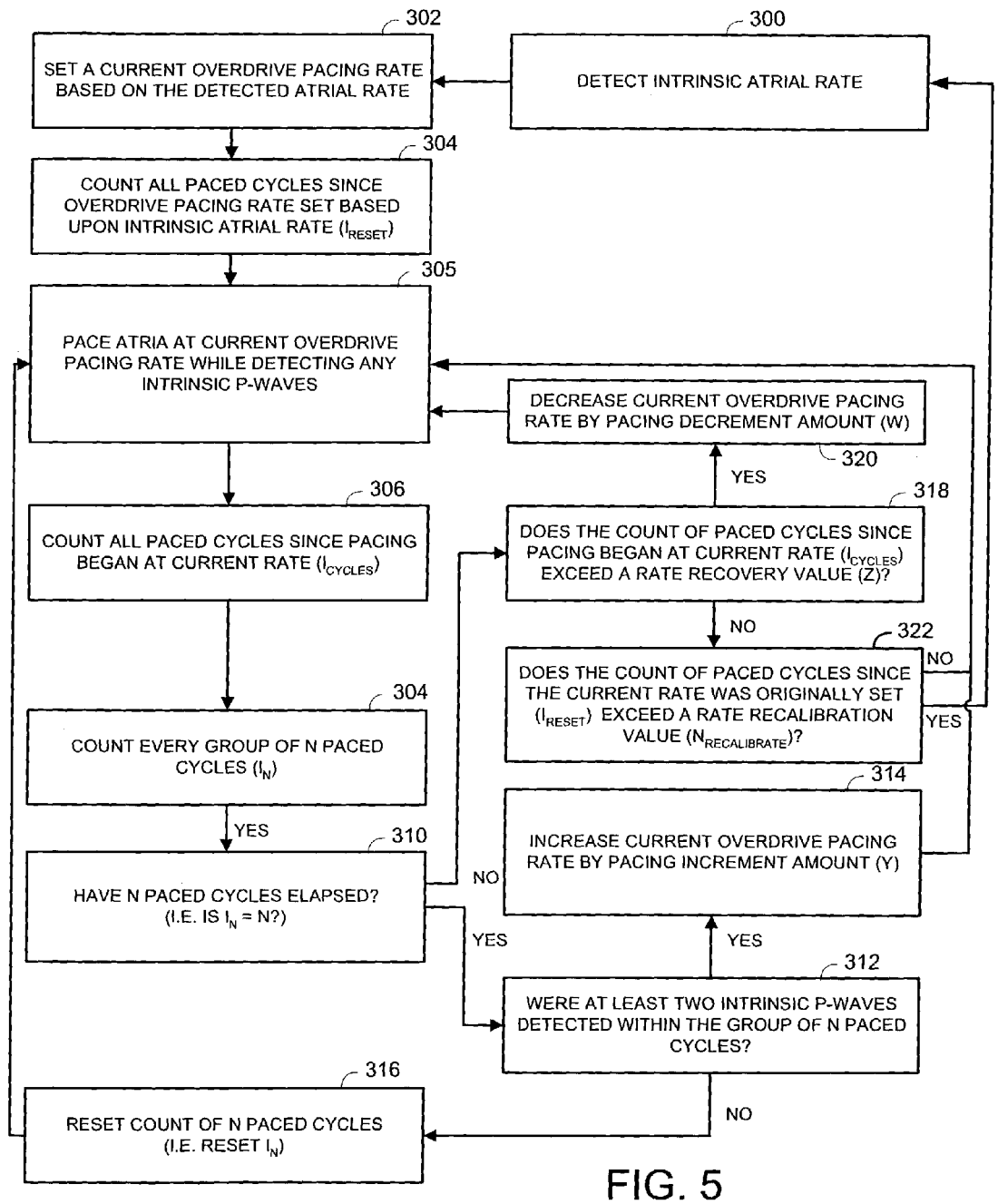
FIG. 5 is a flow chart illustrating a DAO pacing method wherein an overdrive pacing rate is increased only if at least two intrinsic heart beats are detected within a block of N consecutive cardiac cycles.

What have been described thus far with respect to FIG. 5 are circumstances wherein no intrinsic P-waves are detected. In the following, steps performed in response to the detection of P-waves will now be described. More specifically, if at step 212 an intrinsic P-wave is detected, then step 220 is performed wherein a determination is made as to whether a count has already begun of the number of overdrive pacing cycles since detection of the last detected P-wave. During the first execution of step 220 following detection of the first P-wave, the count has not yet begun and hence processing continues to step 222 wherein the cardiac stimulation device begins to count the number of overdrive pacing cycles since the last detected P-wave ($I_{P\text{-}WAVE}$). Processing then returns to step 208 for additional pacing at the current overdrive pacing rate while incrementing $I_{P\text{-}WAVE}$ (along with $I_{RESET}$ and $I_{CYCLES}$) with each additional pacing cycle.

If another P-wave is detected at step 212, then execution proceeds through step 220 to step 224 wherein $I_{P\text{-}WAVE}$ is compared with a pacing cycle increment value (X). If $I_{P\text{-}WAVE}$ is less than X, indicating that the last two detected intrinsic P-waves are within X cardiac cycles of one another, then step 226 is performed wherein the current overdrive pacing rate is increased by a predetermined pacing increment amount (Y) set to, for example, 5, 10, 15, 20, or 25 ppm. Thereafter, pacing continues from step 208 at the new higher overdrive pacing rate. If, however, at step 224, $I_{P\text{-}WAVE}$ was found to be greater than X, meaning that the last two detected intrinsic P-waves were more than X cycles apart, then the overdrive pacing rate is not immediately increased. Instead, processing proceeds to step 222 wherein $I_{P\text{-}WAVE}$ is reset to begin a new count of the number of overdrive pacing cycles since the most recently detected P-wave.

Thus, FIG. 5 is a flow chart illustrating one technique for implementing an overdrive pacing algorithm which, among other features, (1) increases an overdrive pacing rate if two P-waves are detected within X cardiac cycles of one another; (2) decreases the overdrive pacing rate if a rate increase does not occur within at least Z cardiac cycles; and (3) resets the overdrive pacing rate to be equal to a detected sinus rate every $N_{RECALIBRATION}$ number of cardiac cycles regardless of the extent to which the overdrive pacing rate is modified during the interim.

FIG. 5 illustrates a method for controlling overdrive pacing wherein an overdrive pacing rate is increased only if at least two intrinsic atrial beats are detected within a block of N consecutive cardiac cycles. The technique of FIG. 5 is summarized as follows:

1. At the conclusion of a block of N cardiac cycles, the cardiac stimulation device determines if there is more than one P-wave in the block of cardiac cycles, if there is more than one P-wave, the rate is increased by Y ppm.
   a) Y is a programmable rate increment and is programmable to 5,10,15, 20 or 25 ppm.
2. If Z cardiac cycles occur without increasing the rate, then the rate decays at W ppm/cardiac cycle.
   a) Z is the dwell time before the rate is decreased and is programmable from 8 to 40 cardiac cycles.
   b) W is programmable at 1, 2, 3, 4, or 5 ppm/cardiac cycle.

Additionally, the cardiac stimulation device periodically suspends pacing to detect the intrinsic atrial rate and compares to the atrial rate with a current overdrive pacing rate. If the difference between the atrial rate and the overdrive pacing rate exceeds a predetermined threshold ($N_{THRESHOLD}$), then the overdrive rate is reset to the detected atrial rate. Otherwise, overdrive pacing continues at the current pacing rate.

The technique will now be described in greater detail with continued reference to FIG. 5. Certain steps of FIG. 5 are similar to those of FIG. 4 and, accordingly, will not be re-described in detail. Initially, at steps 300 and 302, the cardiac stimulation device detects the current intrinsic atrial rate and sets a current overdrive pacing rate based on the detected atrial rate. Initially, the overdrive rate is set to be equal to the detected atrial rate. During subsequent iterations of steps 300 and 302, the overdrive rate is set to the atrial rate only if the atrial rate minus the current overdrive rate exceeds $N_{THRESHOLD}$.

At step 304, the cardiac stimulation device begins to count all paced cycles ($I_{RESET}$) since the overdrive pacing rate was set at step 302. At step 305, the cardiac stimulation device paces the atria at the current overdrive pacing rate while detecting any intrinsic P-waves. At step 306, all paced cycles since pacing began at the current rate are detected and counted ($I_{PACED}$). At step 308, the cardiac stimulation device also counts every group of N consecutive paced cycles ($I_N$) wherein N is, for example, ten. Initially, the counts initiated at steps 302, 306 and 308 will be the same. As will be seen, however, these counts may diverge from one another with further processing of the method steps.

At step 310, the cardiac stimulation device determines whether N pacing cycles have elapsed by examining $I_N$. If $I_N$ equals N, then step 312 is performed wherein the cardiac stimulation device determines whether at least two intrinsic P-waves have been detected within the group of N paced cycles. If so, then the current overdrive pacing rate is increased at step 314 by an amount Y wherein Y is equal to, for example, 5, 10,15, 20 or 25. Thereafter, processing returns to step 305 for additional atrial pacing at the new overdrive pacing rate. If, at step 312, at least two intrinsic P-waves were not detected within the group of N paced cycles, then step 316 is performed wherein the count of N paced cycles ($I_N$) is reset such that the next set of N consecutive paced cycles may be counted. In this manner, the overdrive pacing rate is increased if, and only if, at least two P-waves are detected within a group of N consecutive cardiac cycles.

If, at step 310, N paced cycles have not yet elapsed (i.e., the count $I_N$ is less than N), then step 318 is performed wherein the cardiac stimulation device determines whether the count of paced cycles since pacing began at the current rate ($I_{PACED}$) exceed a rate recovery value (Z). If so, then at step 320, the overdrive pacing rate is decreased by a pacing decrement amount W wherein W is preset to, for example, 1, 2, 3, 4 or 5. Hence, if the overdrive pacing rate has not been increased as a result of the detection of at least two P-waves within a block of N cycles, then the overdrive pacing rate is decreased to provide rate recovery.

If, at step 318, $I_{PACED}$ does not exceed a Z, then step 322 is performed wherein the cardiac stimulation device determines whether the count of paced cycles since the current rate was originally set ($I_{RESET}$) exceeds a rate calibration value $N_{RECALIBRATION}$. If so, then steps 300 and 302 are repeated wherein overdrive pacing is suspended to permit detection of the intrinsic atrial rate and the overdrive pacing rate is then set based upon the intrinsic atrial rate. As noted above, within step 302, a determination is made as to whether the difference between the intrinsic atrial rate and the overdrive pacing rate exceeds a threshold $N_{RESET\ THRESHOLD}$ and, if not, the overdrive pacing rate is not reset to be equal to the atrial rate. If, at step 322, $I_{RESET}$ does not exceed $N_{CALIBRATION}$, then processing merely returns to step 304 for additional pacing at the current overdrive pacing rate.

Thus, FIG. 5 illustrates an overdrive pacing technique wherein, among other features, (1) an overdrive pacing rate is increased only if at least two P-waves are detected within a block of N consecutive cardiac cycles; (2) the overdrive pacing rate is decreased if the overdrive rate is not increased within Z consecutive cardiac cycles; and (3) the overdrive pacing rate is periodically reset to an intrinsic atrial rate if the difference between the atrial rate and the current overdrive rate exceeds a predetermined threshold. By increasing the overdrive pacing rate only in response to the detection of at least two P-waves within a block of N consecutive cardiac cycles, excessively aggressive overdrive pacing rate increases are avoided. Additionally, with appropriate selection of N, a minimum percentage of paced cycles can be achieved on the average. For example, by setting N equal to ten, the average percentage of paced cycles will be maintained at about 90%. If more than ten percent of the cardiac cycles are intrinsic cycles, then the overdrive pacing rate is increased. Otherwise, the overdrive pacing rate is periodically decreased. Hence, an average of about 90% is sustained.

2. Adaptive DAO Techniques

Figure 6:
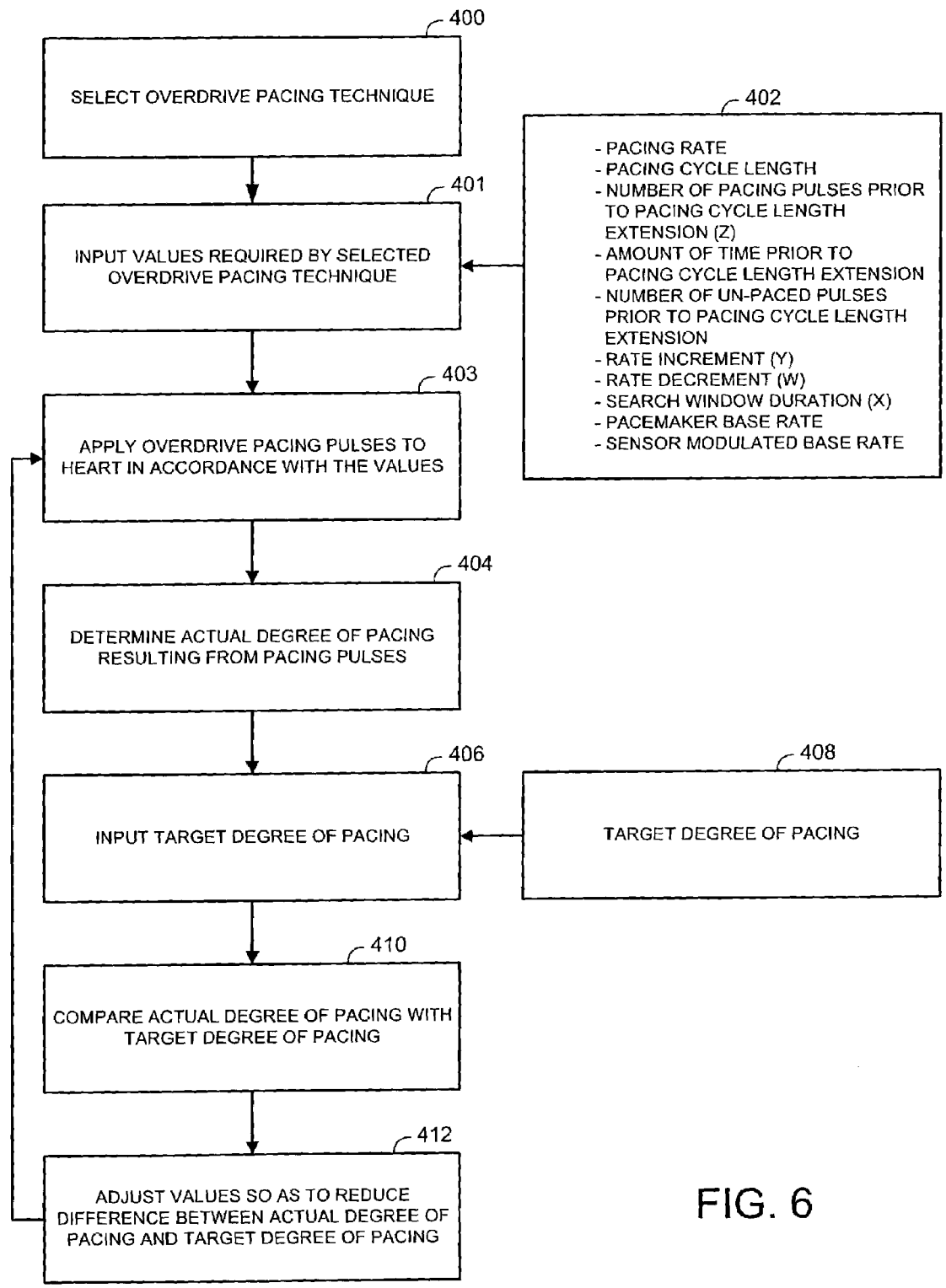
FIG. 6 is a flow chart illustrating a DAO method for adaptively varying programmable values defining overdrive pacing characteristics so as to maintain a target degree of pacing.

With reference to FIG. 6, techniques for adaptively varying overdrive pacing characteristics are summarized. Initially, at step 400, a particular overdrive pacing technique or algorithm is selected by the cardiac stimulation device then, at step 401, programmable values required by the algorithm are input from a memory 402. (If the implantable cardiac stimulation device is capable of performing only a single overdrive pacing technique, step 400 is not necessary.) Depending upon the overdrive pacing technique, the programmable values may be representative of: an overdrive pacing rate; an overdrive pacing margin; a pacing cycle length; a number of pacing pulses prior to pacing cycle length extension (Z); an amount of time prior to pacing cycle length extension; a number of un-paced pulses prior to pacing cycle length extension; a magnitude of rate increments (Y); a magnitude of rate decrement (W); a search window duration (X); a pacemaker base rate; and a sensor modulated base rate.

At step 403, the cardiac stimulation device applies overdrive pacing pulses to the heart in accordance with the requisite programmable values. While overdrive pacing is performed, the cardiac stimulation device performs steps 404-412 to adjust the programmable values so as to reduce any difference between an actual degree of pacing and a target degree of pacing. More specifically, at step 404, the cardiac stimulation device determines the actual degree of pacing resulting from the pacing pulses. The actual degree of pacing may be represented by a percentage of paced pulses (determined as a function of time or as a function of cardiac cycles), or by any other appropriate factor. At step 406, a target degree of pacing is input from a memory 408 and, at step 410, the cardiac stimulation device compares the actual degree of pacing with the target degree of pacing. At step 412, the cardiac stimulation device adjusts the values used at step 402 so as to reduce any difference between the actual degree of pacing and the target degree of pacing. The specific adjustment depends upon a particular programmable value being adjusted. In some cases, the value may need to be increased so as to cause a decrease in the degree of pacing. In other cases, the value may need to be decreased so as to cause a decrease in the degree of pacing. The direction of the adjustment and the magnitude of the adjustment are set so as to achieve a negative feedback loop which converges the actual degree of pacing to the target degree of pacing. To this end, routine experiments are performed to determine optimal values for adjusting the various parameters to achieve the desired feedback loop and to eliminate adjustment values, if any, which may result in a positive feedback loop causing the actual degree of pacing to deviate from the target degree of pacing, rather than to converge to the target degree of pacing. The resulting adjustment in the values may be linear or non-linear, depending upon the particular programmable values and depending upon the amount of difference, if any, between the actual degree of pacing and the target degree of pacing. As can be appreciated, a wide range of possible adjustments can be employed depending upon the characteristics of the overdrive pacing technique being implemented. In many cases, two or more programmable values are adjusted simultaneously. For example, both the overdrive pacing margin and the number of pacing pulses prior to a pacing cycle length extension may be adaptively adjusted.

A first specific example of the technique of FIG. 6 will now be described with reference to FIG. 7. In this specific example, the cardiac stimulation device operates to maintain the overdrive pacing rate at a rate equal to the intrinsic rate plus a programmable rate margin. The rate margin is adaptively varied so as to maintain a target degree of pacing. Initially, at step 500, the cardiac stimulation device inputs an initial overdrive pacing margin from a memory unit 502. The margin may be, for example, five pulses per minute (ppm)—indicating that the heart is to be paced at a rate equal to the intrinsic heart rate plus five ppm. At step 504, the cardiac stimulation device periodically determines the intrinsic heart rate and administers overdrive pacing pulses to the heart at a rate equal to the intrinsic rate plus the overdrive pacing margin. For example, if the intrinsic rate is found to be 60 beats per minute (bpm), the cardiac stimulation device overdrive paces the heart at a rate of 65 ppm. If the intrinsic rate is found to increase to 80 bpm, then the overdrive pacing rate automatically increases to 85 ppm. In this manner, the cardiac stimulation device seeks to maintain the overdrive pacing rate at a rate slightly higher than the intrinsic rate at all times.

A determination of the intrinsic rate at step 504 may be performed, for example, by periodically deactivating overdrive pacing thereby permitting detection of intrinsic beats from which the intrinsic heart rate is determined. In this regard, an estimate of the intrinsic heart rate may be calculated based upon the duration of time between the detected intrinsic beats. The greater the number of intrinsic beats that are detected, the more precise the determination of the intrinsic heart rate.

Step 506 is periodically performed wherein the cardiac stimulation device counts the number of paced pulses and the number of un-paced pulses until a predetermined period of time, such as 60 seconds, has elapsed. Alternatively, the cardiac stimulation device counts the pulses until a predetermined number of total pulses, such as 100 pulses, have been counted. The cardiac stimulation device then calculates a percentage of the number of paced pulses out of a total number of pulses. In the example of FIG. 3, with nine paced beats and one un-paced beat, the percentage of paced beats is about 90%. At step 508, the cardiac stimulation device inputs a target degree of pacing from a memory unit to ten. The target of pacing may be, for example, 95% paced beats. At step 510, the cardiac stimulation device determines whether the actual percentage of paced beats determined at step 506 is greater than the target percentage of paced beats input at step 508. If so, then step 512 is performed wherein the cardiac stimulation device automatically decreases the overdrive pacing margin by a predetermined amount, such as one ppm. If not, then the cardiac stimulation device automatically increases the overdrive pacing margin by the predetermined amount at step 516.

Thereafter, step 504 is performed using the adjusted overdrive pacing margin. Hence overdrive pacing may now occur at a rate of six ppm above the intrinsic rate or perhaps only at a rate of four ppm above the intrinsic rate. With repeated iterations of steps 506-514, the degree of overdrive pacing is thereby periodically, adaptively adjusted so as to maintain the actual percentage of paced pulses at an amount about equal to the target degree of pacing, e.g., at about 95%. Hence, if the initial overdrive pacing adjustment factor was too high such that substantially 100% of heart beats were paced beats, the overdrive facing adjustment factor is decreased somewhat to permit occasional detection of an unpaced beat. This helps ensure that the overdrive pacing rate is not so high so as to possibly adversely affect the health of the patient. Also, avoidance of an unnecessarily high overdrive pacing rate helps preserve battery longevity. Moreover, in embodiments wherein the cardiac stimulation device relies upon detection of an occasional intrinsic beat so as to determine the intrinsic heart rate, a reduction of the overdrive pacing rate helps ensure that intrinsic beats are occasionally detected. On the other hand, if the actual degree of overdrive pacing was found to be significantly less than 95%, then the overdrive pacing rate is increased so as to prevent too many intrinsic bits from occurring which might trigger a tachyarrhythmia.

Figure 7:
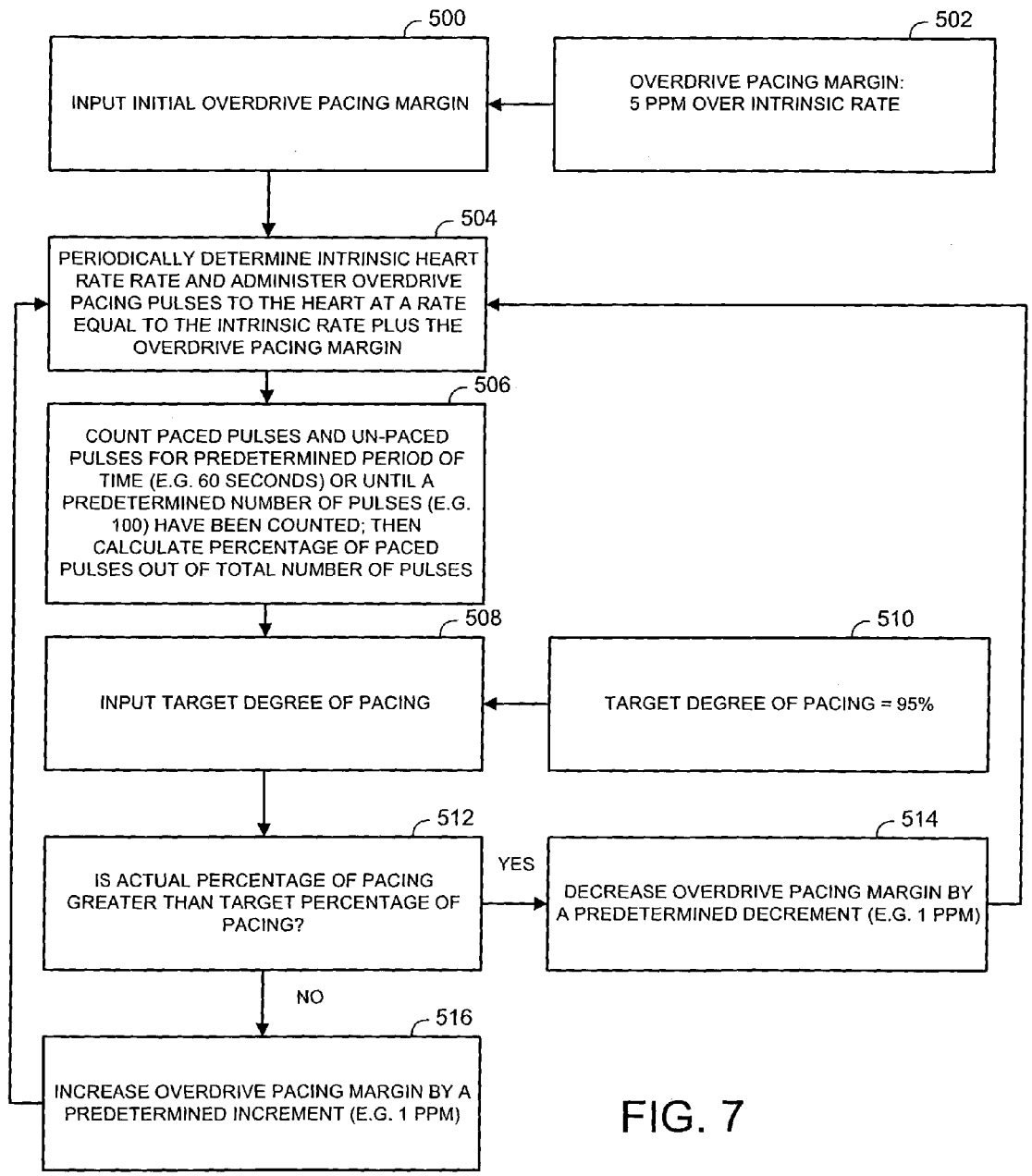
FIG. 7 is a flow chart of the DAO method of FIG. 6 configured for adaptively varying an overdrive pacing rate.

Although not specifically shown in FIG. 7, if, at step 510, the actual percentage of pacing is found to be exactly equal to the target degree of pacing, then the cardiac stimulation device may be configured to not adjust the overdrive pacing adjustment factor either up or down. Also, the predetermined amount by which the overdrive pacing margin is increased may differ from that in which it is decreased. Also, the predetermined amounts may vary depending upon the current overdrive pacing rate or upon the current overdrive pacing adjustment factor. For example, if the overdrive pacing margin is currently set to 20 ppm, the factor may be increased or decreased by a greater amount than if the factor was currently set to two or three ppm. Likewise, if the current overdrive pacing rate (i.e., the sum of the current intrinsic heart rate and the current overdrive pacing adjustment factor) is particularly high, then the predetermined amounts may also be relatively high. Also, note that the overdrive pacing margin may be negative, at times. As can be appreciated, a wide range of alternatives may be provided.

Another specific example of the technique of FIG. 6 will now be described with reference to FIG. 8. In this specific example, the cardiac stimulation device performs an dynamic atrial overdrive technique wherein detection of a single P-wave triggers an immediate, significant increase in the overdrive rate and wherein, after an increase, the pacing cycle length is periodically extended to a gradual reduction in the overdrive pacing rate. More specifically, the dynamic atrial overdrive technique operates as follows. The cardiac stimulation device monitors the atria of the heart and detects P-waves and, in response to detection of a single P-wave, increases the overdrive pacing rate by a programmable increment value which depends upon whether the current overdrive base rate is within: a lower rate overdrive (LRO) regime of 25 and 59 ppm; a middle rate overdrive regime (MRO) of 60 and 149 ppm; or an upper rate overdrive (URO) of 150 and 185 ppm.

Within the LRO regime, the stimulation device increases the overdrive rate with each sensed P-wave by an LRO increment programmable to values of 5, 10, 15, 20 and 25 ppm. Within the URO regime, the stimulation device increases the overdrive rate with each sensed P-wave by a URO increment programmable to values of 5 or 10 ppm. (Typically, the LRO increment value is programmed to a high value, such as 25 ppm, whereas the URO increment is programmed to a low value such as 5 ppm.) Within the MRO regime, the stimulation device increases the overdrive rate with each sensed P-wave by an MRO increment which is a blended value between the LRO increment and the URO increment. The MRO increment is equal to the LRO increment when the base rate is 60 ppm. The MRO increment varies gradually when the base rate is in the range of 60 ppm to 150 ppm until the increment is equal to the URO increment when the base rate is equal to 150 ppm.

The stimulation device also exploits a dynamic rate recovery technique wherein the overdrive base rate is decreased if a pre-determined number of pacing cycles occur without any detected P-waves. The pre-determined number of cycles and the amount of the decrease are both programmable. The amount of the decrease varies depending upon whether the base overdrive pacing rate is within one of two regimes.

The specific operation of the stimulation device within the various regimes is described with reference to the following examples.

As an example of operation within the LRO regime, if the current overdrive rate is 45 ppm, the LRO increment value is 5 ppm, and a P-wave is sensed, the current overdrive pacing rate is immediately increased to 50 ppm. If the P-wave arises from intrinsic atrial activity occurring at a rate of 53 bpm, then a second P-wave will be detected before a paced beat can be generated (because the overdrive base rate is still below the intrinsic rate). Hence, another P-wave is detected and the overdrive pacing rate increases to 55 ppm.

As an example of operation within the LRO regime, if the current overdrive pacing rate is 55 ppm, the LRO increment is 25 ppm, the URO increment is 5 ppm, and the patient experiences an SVT at 160 bpm, then the overdrive pacing rate increases by 25 ppm with each sensed atrial beats until it exceeds a 60 ppm, then any further increments begin at slightly less than the LRO increment of 25 ppm and are gradually reduced to the URO increment of 5 ppm at a 150 ppm.

To provide rate recovery, the cardiac stimulation device counts the number of pacing pulses delivered at a current overdrive rate and, if the number of cycles exceeds a threshold value $N_{MAX}$, the cardiac stimulation device decreases the overdrive pacing rate by increasing a pacing cycle length (CL) equal to the amount of time between individual pacing pulses. $N_{MAX}$ is programmable within a range of 1 to 16 cycles. Thus, if $N_{MAX}$ is programmed to 10 cycles and the overdrive pacing rate has remained constant for 10 cycles, then the CL is increased by a programmable rate recovery value. In this manner, so long as no intrinsic activity is detected, the overdrive rate gradually decreases. Whenever intrinsic atrial activity is sensed, the counter associated with $N_{MAX}$ is reset and, in accordance with the techniques already described, the overdrive pacing rate is incremented. Exemplary programmable CL increment values are:

6;13 milliseconds/cycle
6;19 milliseconds/cycle
13; 19 milliseconds/cycle
19;25 milliseconds/cycle As noted, an increase in the pacing cycle length causes a corresponding decrease in the overdrive pacing rate. In the foregoing, the first value represents the increase in CL in milliseconds per cycle to be used if the current base rate is over 100 ppm. The second value represents the increase in CL in milliseconds per cycle to be used if the current base rate is 100 ppm or less. Thus, two base CL increment regimes are used.

In a specific rate recovery example, if the current overdrive rate is 102 ppm, the intrinsic atrial rate is 90 ppm, and the dynamic rate recovery values are programmed to 6;19 milliseconds/cycle, then the pacing cycle length decreases after every $N_{MAX}$ follows:

(1) 595 milliseconds (101 ppm)
(2) 601 milliseconds (100 ppm)
(3) 620 milliseconds (97 ppm)
(4) 639 milliseconds (94 ppm)
(5) 658 milliseconds (91 ppm)

Thus, the cardiac stimulation device employs a dynamic atrial overdrive technique which increases an overdrive base rate very promptly in response to detection of intrinsic atrial activity (i.e. P-waves) and provides a rate recovery technique for reducing the overdrive pacing rate when overdrive pacing is no longer needed. The degree of increment or decrement to the overdrive pacing base rate depends, as described, upon the current base rate regime. Additional variations to the overdrive pacing rate may be based upon detection of pre-atrial contractions (PAC) or other intrinsic events.

Figure 8:
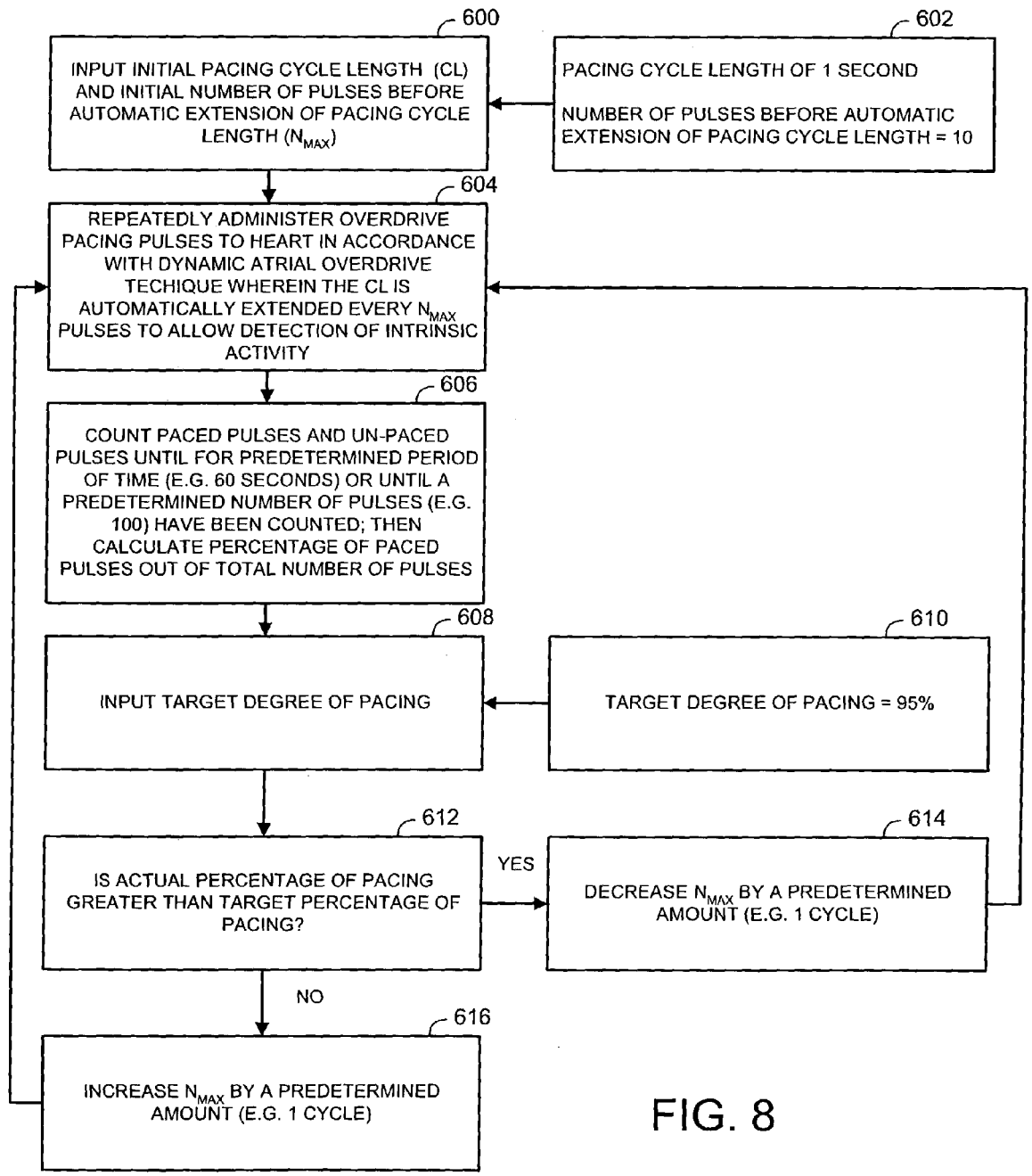
FIG. 8 is a flow chart illustrating a method for adaptively modifying the automatic pacing cycle length adjustment to maintain a target degree of pacing.

In the technique of FIG. 8, $N_{MAX}$ is adaptively varied to maintain a target degree of pacing. Initially, at step 600, the cardiac stimulation device inputs both an initial pacing cycle length (CL) and $N_{MAX}$ from a memory unit 602. CL may be, for example, one second (corresponding to an overdrive pacing rate of 60 ppm) and $N_{MAX}$ may be, for example, set initially to ten.

At step 604, the cardiac stimulation device repeatedly administers overdrive pacing pulses to the heart in accordance with the dynamic atrial overdrive algorithm described above wherein the CL is automatically extended every $N_{MAX}$ pulses to allow occasional detection of intrinsic heart beats or other intrinsic activity. While step 604 is performed, the cardiac stimulation device additionally performs steps 606-616 as follows. The cardiac stimulation device counts the number of paced pulses and un-paced pulses for either a predetermined period of time or a predetermined number of pulses then calculates the percentage of paced pulses at step 606. A target degree of pacing is input at step 608 from a memory 610 and, at step 612, the cardiac stimulation device determines whether the actual percentage of pacing is greater than the target percentage of pacing. If so, then $N_{MAX}$ is decreased by a predetermined amount, such as one cycle, at step 614. If not, then $N_{MAX}$ is increased by a predetermined amount, such as one cycle, at step 616. Thereafter, the overdrive pacing performed by the cardiac stimulation device during step 604 is performed using the adjusted value for $N_{MAX}$. With repeated iterations of steps 606-616, the actual degree of pacing is maintained substantially at or near the target degree of pacing so as to prevent excessive overdrive pacing while still minimizing the number of non-paced beats. In this regard, $N_{MAX}$ is decreased when the actual percentage of pacing is greater than the target percentage of pacing so as to permit a more prompt detection of an intrinsic pulse from which a new intrinsic heart rate is determined. By permitting a more prompt detection of a next intrinsic beat, the overdrive pacing rate can thereby be adjusted, in accordance with the dynamic atrial overdrive algorithm, to match more closely the intrinsic rate. In contrast, by increasing $N_{MAX}$ if the actual percentage of pacing is found to be less than 95%, a greater amount of time elapses prior to detection of a next intrinsic pulse thereby delaying readjustment of the overdrive pacing rate. This may result in a generally higher overdrive pacing rate. In any case, regardless of whether the adjustments to $N_{MAX}$ result in an increase or decrease in the overall average overdrive pacing rate, the adjustments to $N_{MAX}$ will typically operate to maintain the percentage of paced beats at about the target percentage and the advantages set forth above are achieved.

In another specific example of the technique of FIG. 6, the implantable cardiac stimulation device employs a technique for modulating the base rate of the device based upon circadian rhythms of the patient. The technique for modulating the base rate is described in U.S. Pat. No. 5,476,483 to Bornzin et al. which is incorporated by reference herein. Briefly, in accordance with the technique of the circadian patent, the base rate associated with a transfer function of a rate-responsive cardiac pacemaker is modulated. Activity sensor measurements are used to derive activity variance measurements, which in turn are used to modulate the base pacing rate. In one embodiment, a histogram is used to store activity variance measurements collected over a period of about one week. A histogram is used to derive an activity variance threshold, which is compared to current activity variance measurements to determine if the patient is asleep. If the patient is deemed to be asleep, the pacing rate is set to a rate that comfortably meets the low metabolic demands of the patient during sleep. In alternative embodiments, the activity variance measurements are applied to a base rate slope to modulate the base pacing rate.

Thus, the base rate can be modulated and as such, the percentage of time that underlying, intrinsic P-waves are detectable during a search period can be adjusted by adaptively adjusting the base rate in accordance with the adaptive techniques described above. With proper selection of appropriate adaptive adjustment values, when the cardiac stimulation device extends an atrial escape interval to permit detection of an underlying, intrinsic P-wave, the adjusted base rate will limit the extension of the escape interval so that the base rate is in fact higher than the underlying atrial rate. Accordingly, there will be few, if any, emerging P-waves. More specifically, parameters sleep rate and BPR_slope within Equation 9 of the Bornzin, et al. Patent are adaptively adjusted so as to achieve a target degree of pacing. Increasing sleep rate and BPR_slope has the effect of increasing the base rate and thus increasing the percentage of atrial pacing.

Dynamic Ventricular Overdrive Techniques

Figure 9:
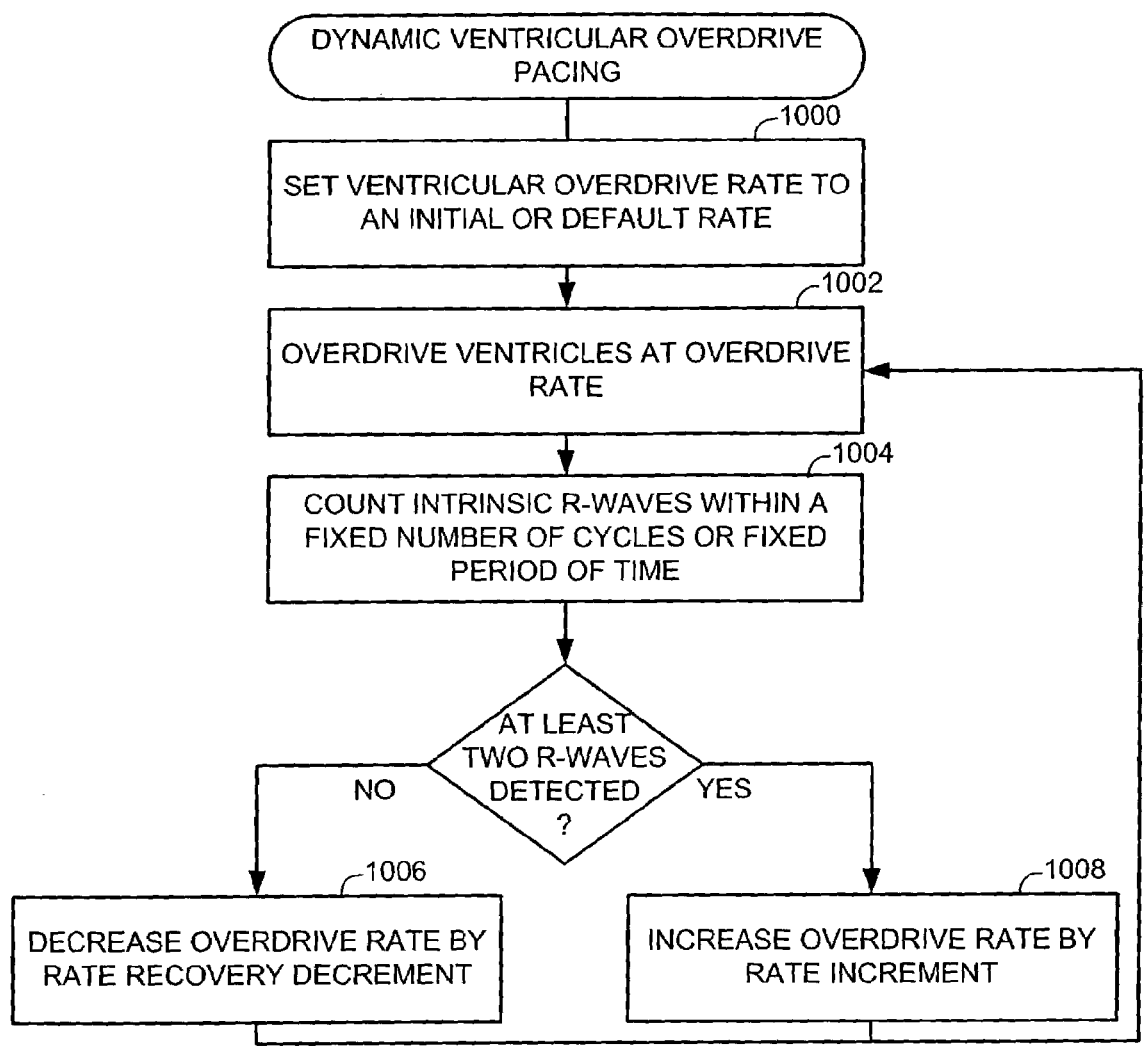
FIG. 9 is a flow chart illustrating, at a high level, an illustrative embodiment of a DVO method employed by the stimulation device of FIGS. 1 and 2.
Figure 16:
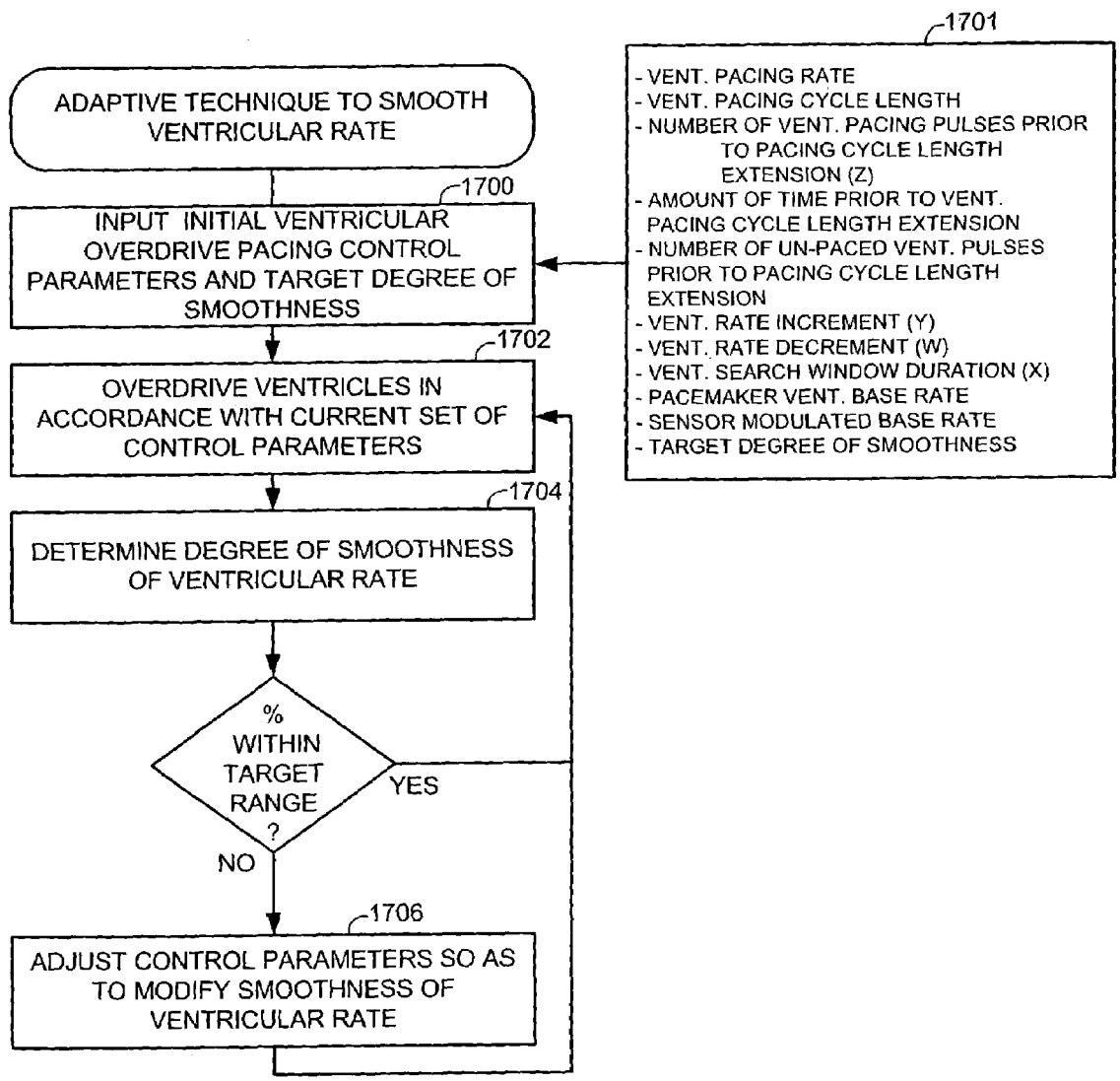
FIG. 16 is a flow chart illustrating an adaptive DVO pacing method for smoothing the ventricular rate.
Figure 17:
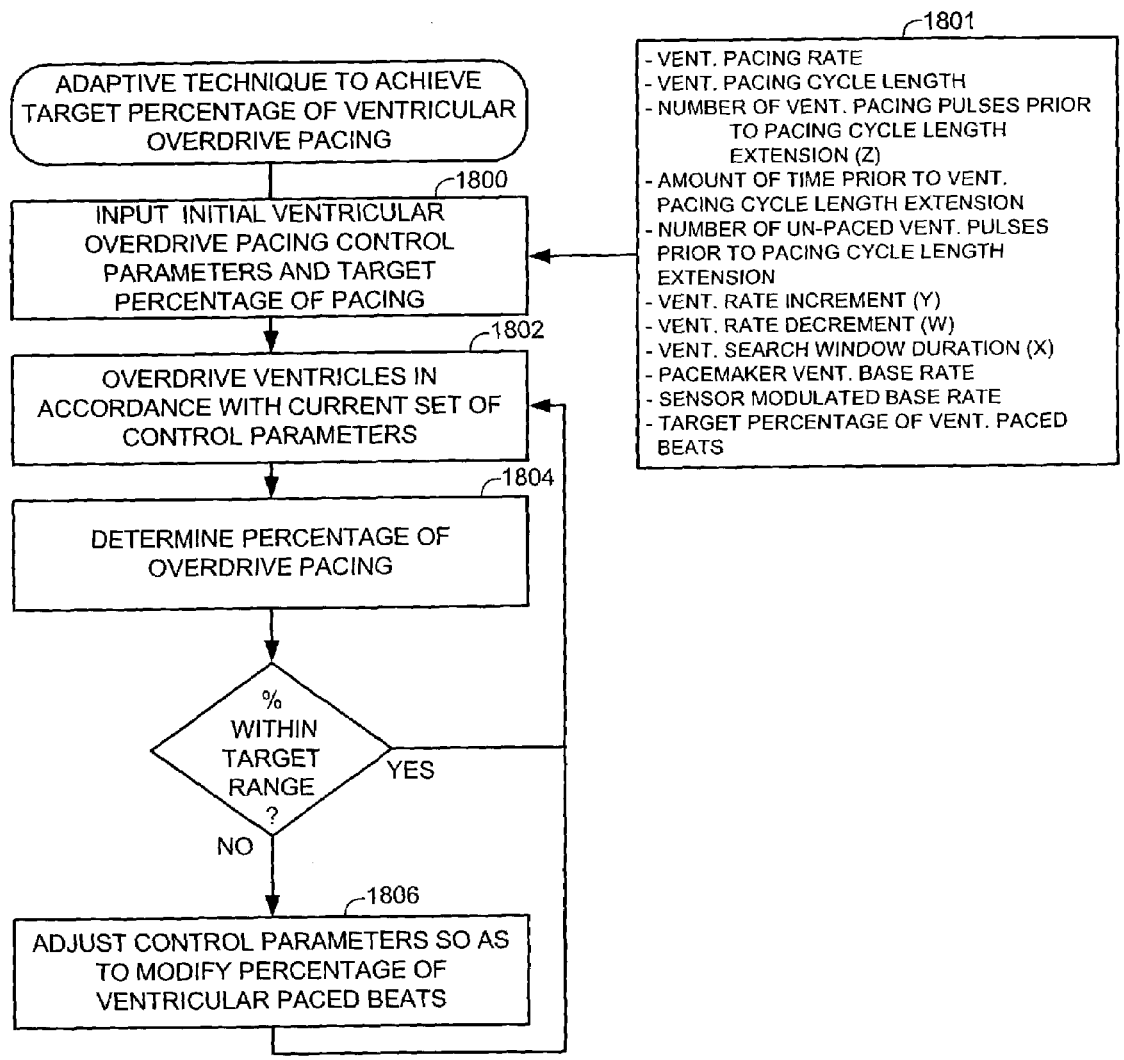
FIG. 17 is a flow chart illustrating an adaptive DVO pacing method for achieving a target percentage of ventricular overdrive pacing.

With reference to the remaining figures, various exemplary methods for performing DVO pacing will be described. FIG. 9 provides an overview of an exemplary technique performed by DVO controller 122 (FIG. 2) for controlling DVO, while it is active. FIGS. 10-15 illustrate, at a high level, techniques for activating and deactivating DVO within various exemplary pacing devices, such as DDD and VVI pacing devices, provided with different sets of internal components, such as AF detectors, PVC density detectors, heart rate stability detectors, etc. Unlike the DAO technique described above, which is preferably performed at all times regardless of the pacing mode, DVO is selectively activated and deactivating based upon the current pacing mode, the presence of atrial fibrillation, and other factors. Rather than separately illustrating and describing the many different possible pacer configurations, the descriptions of FIGS. 10-15 each refer to the multi-chamber device of FIGS. 1 and 2, which includes all pertinent components. It should be understood that, to implement the various methods, not all of the components of the device of FIGS. 1 and 2 are required; rather only a subset of those components are needed. FIGS. 16 and 17 provide adaptive techniques.

1. DVO Overview

FIG. 9 provides an overview of one illustrative embodiment of the DVO technique. Initially, to activate DVO, at step 1000, the DVO controller 122 (FIG. 2) selects an initial ventricular overdrive rate then, beginning at step 1002, the ventricles are paced at the overdrive rate while, at step 1004, intrinsic breakthrough R-waves are detected and counted. So long as at least two intrinsic R-waves have not been detected within a fixed number of pacing cycles (or fixed period of time), the ventricular overdrive rate is periodically decreased by a ventricular recovery rate decrement, at step 1006, which is typically 2-3 bmp. Once two intrinsic R-waves have been detected, the ventricular overdrive rate is bumped back up, at step 1008, by a rate increment, which, in this example, is set to a programmed value in the range of 5 to 25 bpm. Then periodic rate decrements are again performed until at least two more intrinsic R-waves have been detected. In this manner, the ventricular overdrive rate is maintained at a rate slightly above the intrinsic ventricular rate so as to provide a high percentage of overdrive paced beats or a high degree of rate smoothing. Note that the initial overdrive rate selected at step 1000 may be set to a programmed default rate, such as 80 bpm. Alternatively, it may be set based on an actual, calculated intrinsic ventricular rate. However, once DVO has begun, at step 1002, it is no longer necessary to calculate the intrinsic ventricular rate. Rather the DVO controller merely bumps the overdrive rate up or down based upon the count of intrinsic ventricular breakthrough events made at step 1004.

Briefly, the foregoing technique can be summarized as follows:

1. Identify R-wave.
2. If another R-wave occurs within $X_{VENT.}$ cardiac cycles (or within $X_{VENT.}$ amount of time), increase pacing rate by $Y_{VENT.}$ bpm.
   a) $X_{VENT.}$ is programmable from about 20 to 60 ventricular cycles.
   b) $Y_{VENT.}$ is the programmable rate increase and is programmable from 2-25 ppm.
3. If $Z_{VENT.}$ ventricular cycles occur without a rate increase, then decrease rate by W ppm/cardiac cycle.
   a) $Z_{VENT.}$ is the dwell time before rate is decreased and is programmable from 20 to 60 ventricular cycles.
   b) $W_{VENT.}$ is programmable at 1, 2, 3, 4, or 5 ppm/cardiac cycle.

Depending upon the selected parameters, ventricular overdrive pacing can be even more aggressive than the atrial overdrive pacing described above. Also, note that the foregoing merely provides an overview of the DVO technique. In practice, algorithms that are more complex may be employed to control DVO, such as those described above in connection with DAO. Also, for example, rather than using a rate increment set to a programmed value, the increment may instead be defined based upon the slope of a lower overdrive rate to an upper overdrive rate. Further details regarding various overdrive techniques that may be selectively adapted for DVO are provided in: U.S. patent application Ser. No. 10/093,225, of Florio et al., entitled "Method And Apparatus For Using A Rest Mode Indicator To Automatically Adjust Control Parameters Of An Implantable Cardiac Stimulation Device", filed Mar. 6, 2002; U.S. patent application Ser. No. 10/043,781, also of Florio et al., entitled "Method And Apparatus For Dynamically Adjusting A Non-Linear Overdrive Pacing Response Function", filed Jan. 9, 2002; and U.S. patent application Ser. No. 10/043,472, of Falkenberg et a/., entitled "Method And Apparatus For Dynamically Adjusting Overdrive Pacing Parameters", filed Jan. 9, 2002. Capture of overdrive pulses may be verified as set forth in U.S. patent application Ser. No. 10/138,438, of Bradley et al., entitled "Method And Apparatus For Providing Atrial AutoCapture In A Dynamic Atrial Overdrive Pacing System For Use In An Implantable Cardiac Stimulation Device", filed May 2, 2002. Each of the aforementioned patent applications is incorporated herein in their entirety.

In general, the main objective of the dynamic ventricular overdrive techniques described herein is to provide for a reasonably high degree of rate smoothing, as that is typically the most beneficial for patients. In general, the higher the ventricular overdrive rate, the greater degree of rate smoothing. However, the smooth rate is gained at the expense of having a generally higher ventricular rate, which may have certain adverse consequences, both the patient and the pacing device. For the patient, the high ventricular rate can be an annoyance and, depending upon the patient, can exacerbate medical conditions, such as congestive heart failure. For the device, the higher pacing rate more quickly depletes battery power. Accordingly, it is desirable to provide a sufficient degree of rate smoothing so as to achieve its beneficial effects, without providing too high of an average ventricular rate. The optimal degree of rate smoothing is determined by the physician based on the needs of patient. Accordingly, the aforementioned parameters are set by the physician using an external programmer so as to impart a desired degree of smoothness to the overdrive pacing of the ventricles. In one example, the physician sets the parameters during an initial visit with the patient, then evaluates the degree of rate smoothing achieved during a subsequent session with the patient, wherein the physician reviews diagnostic information stored within the device pertaining to the ventricular rate smoothing. Alternatively, as described below with reference to FIGS. 16 and 17, adaptive techniques are provided for automatically adjusting the parameters so as to achieve a target degree of rate smoothing or a target percentage of paced beats.

2. Pacer with AMS

Figure 10:
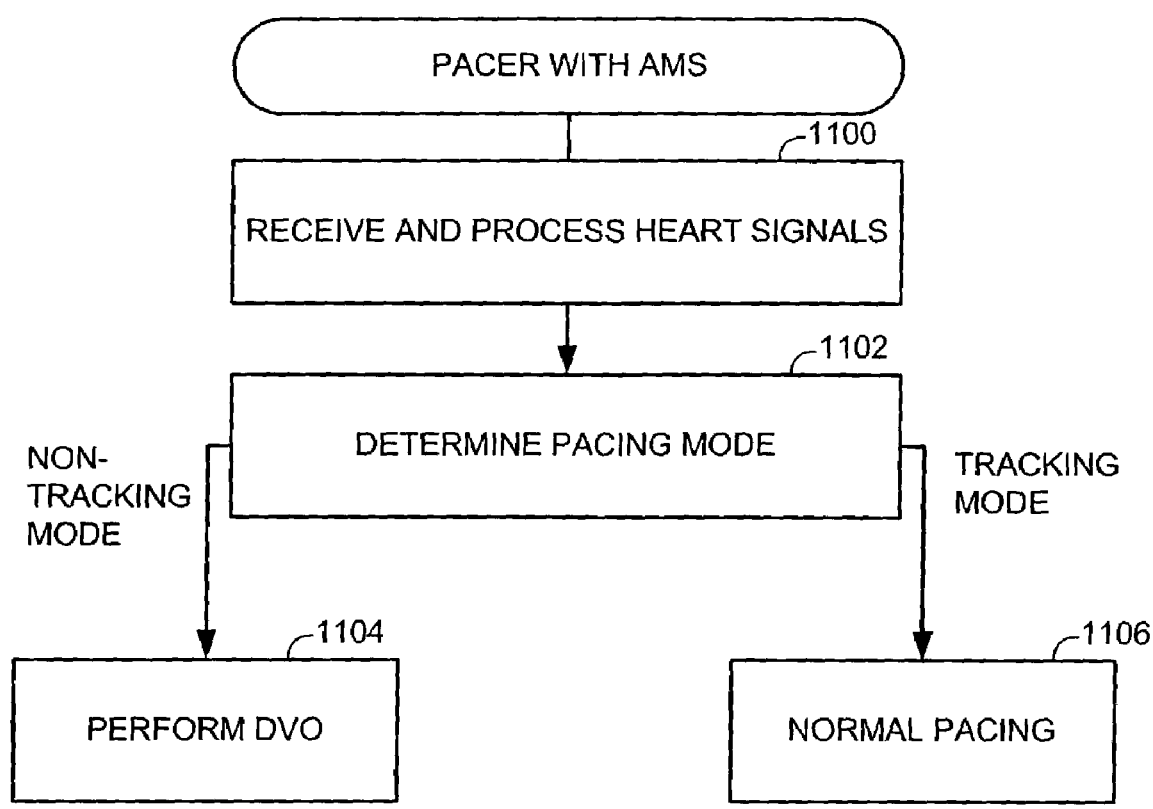
FIG. 10 is a flow chart providing an overview of a first exemplary DVO method wherein the stimulation device of FIGS. 1 and 2 has AMS enabled.

FIG. 10 illustrates a method for activating and deactivating DVO within a pacer capable of AMS. Initially, at step 1100, the microcontroller of the implantable device receives and process electrical signals from the heart and determines the heart rate therefrom. Based on the heart rate, and perhaps other factors, the microcontroller determines at step 1102 whether to perform a mode switch to a DDI or VVI mode, i.e. to switch from a tracking mode to a non-tracking mode. Techniques for implementing AMS are described in U.S. Pat. No. 5,144,949, which is incorporated herein by reference. Whenever the devices switches from a tracking mode to a non-tracking mode, perhaps because the heart rate has exceeded a pre-determined threshold, DVO is activated, at step 1104, under the control of DVO controller 122 (FIG. 2), primarily in an effort to smooth the ventricular rate and thereby preventing any excessively high ventricular rates from occurring, which might trigger a ventricular tachyarrhythmia. If switched from a non-tracking mode to a tracking mode, DVO is deactivated and normal pacing is instead performed, at step 1106, since overdrive pacing the ventricles during a tracking mode (such as DDD) can trigger pacemaker mediated tachycardias (PMT) or other pacemaker induced arrhythmias.

3. DDI Pacer with AF Detector

Figure 11:
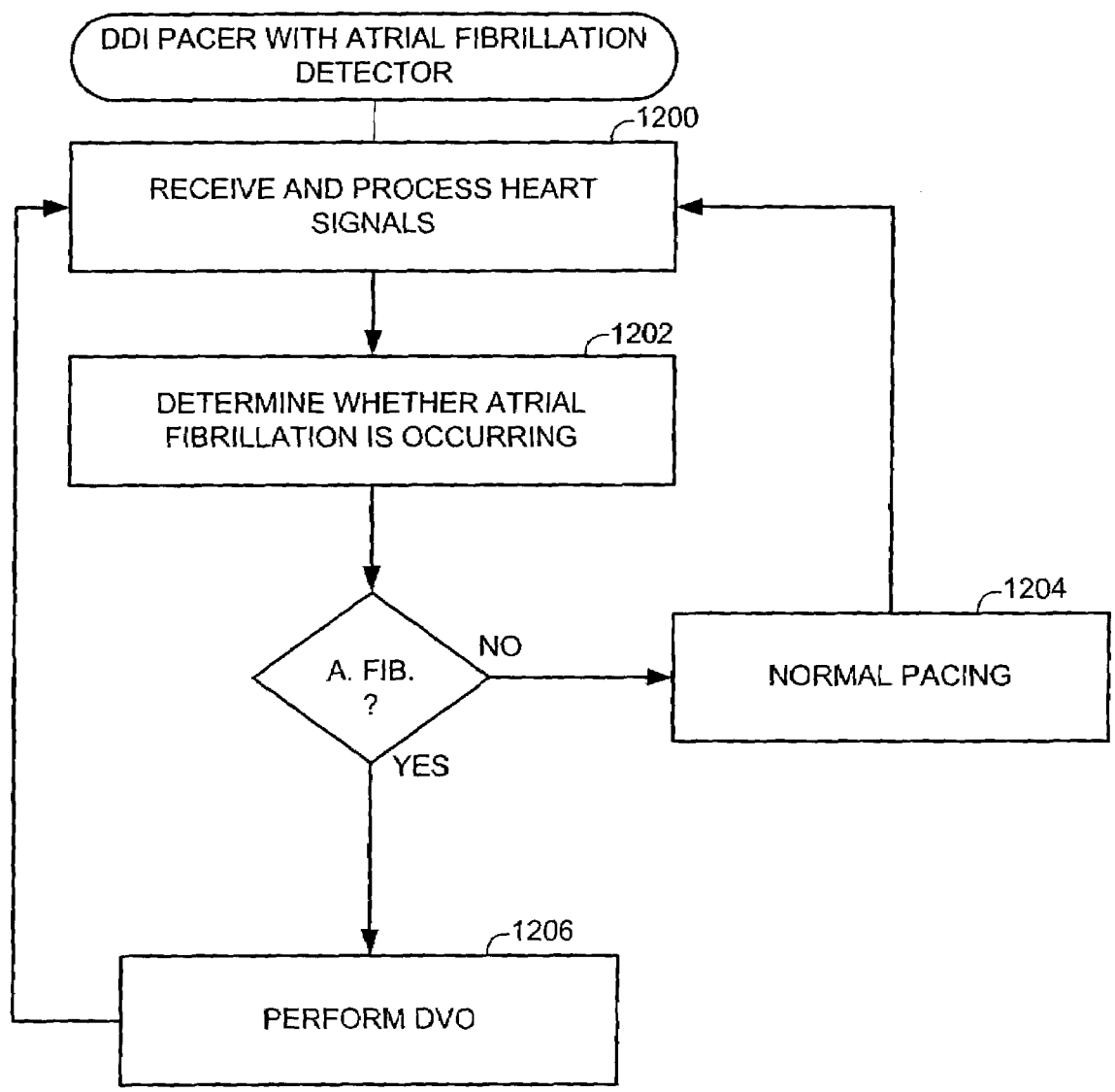
FIG. 11 is a flow chart providing an overview of a second DVO method wherein the stimulation device of FIGS. 1 and 2 operates in a DDI mode with an AF detector enabled.

FIG. 11 illustrates a method for activating and deactivating DVO within a DDI pacer provided with an AF detector (such as AF detector 124 of FIG. 2). At step 1200, the microcontroller of the implantable device receives and process electrical signals from the heart and, at step 1202, employs the AF detector to detect whether the patient is presently suffering from an episode of AF. An AF detector is described in U.S. Pat. No. 5,720,295, which is incorporated herein by reference. If AF is not detected, normal pacing is performed, at step 1204. While AF is occurring, DVO is performed, at step 1206, under the control of DVO controller 122 (FIG. 2) primarily to smooth the ventricular rate during AF and to prevent unnecessarily high ventricular rates from occurring during the AF. Although summarized with respect to and DDI pacer provided with an AF detector, the technique of FIG. 11 may also be performed by a DDD pacer provided with an AF detector, though care should be taken to switch the pacing mode from DDD to DDI or VVI while DVO is performed.

4. DDD Pacer with PVC Density Detector

Figure 12:
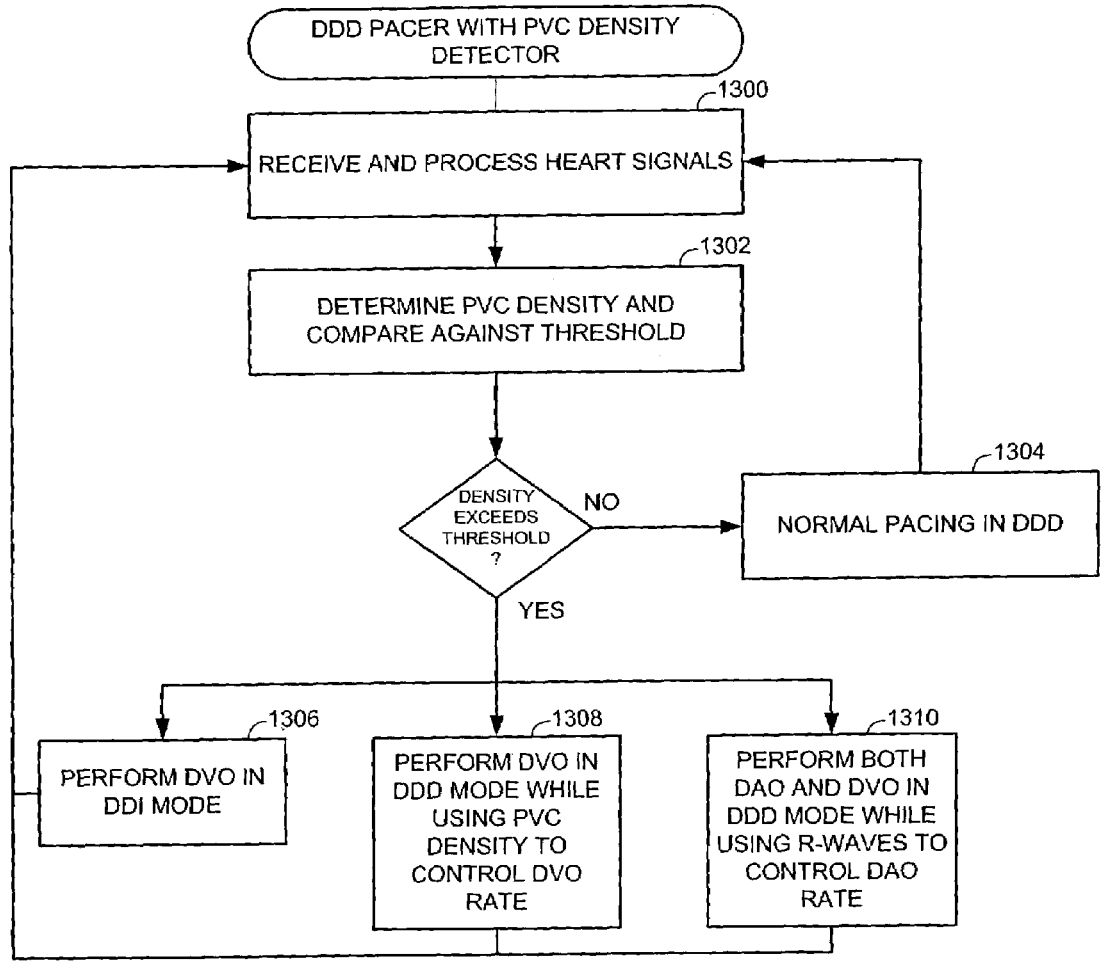
FIG. 12 is a flow chart providing an overview of a third DVO method wherein the stimulation device of FIGS. 1 and 2 operates in a DDD mode with a PVC density detector enabled.

FIG. 12 illustrates a method for activating and deactivating DVO within a DDD pacer provided with a PVC density detector (such as PVC density detector 126 of FIG. 2) for determining the number of PVCs within a given period of time, i.e. to determine the density of PVCs. At step 1300, the microcontroller of the implantable device receives and process electrical signals from the heart and, at step 1302, employs the PVC density detector to determine the PVC density and compare it against a preprogrammed threshold. A PVC is a native depolarization arising from an ectopic location in the ventricle and occurring early with respect to the next expected conducted ventricular depolarization. (A PVC may also be referred to as a ventricular premature beat (VPB) or contraction (VPC) or a ventricular ectopic beat (VEB) or premature ventricular depolarization (PVD).) Within the DDD mode, a PVC is defined as an R-wave following a V-pulse or R-wave, without an intervening A-pulse or P-wave. The PVC density threshold may be programmed by the physician using the external programmer or may be preset within the device. If preset, the PVC threshold is initially determined based on routine studies identifying optimal PVC densities at which to activate DVO. A suitable PVC density threshold is in the range of 3-10 PVCs per minute. PVC detection is described in U.S. Pat. No. 5,097,832, which is incorporated herein by reference.

While the density of PVCs remains below the threshold, DVO remains inactive, at step 1304, since DVO rate smoothing is generally not required while the density of PVCs is low. However, if the density of PVCs exceeds the threshold, DVO is activated in an effort to smooth the ventricular rate so as to decrease the number of PVCs. More specifically, the pacer activates DVO in one of three different programmable modes. In a first mode, shown in step 1306, the pacer is first switched to DDI mode and then DVO is performed in accordance with the standard DVO techniques described herein (wherein the DVO rate is controlled based upon the detection of breakthrough intrinsic ventricular events.) In a second mode, shown in step 1308, the pacer remains in DDD mode and DVO is performed in accordance with an alternative DVO technique wherein the DVO rate is controlled, at least in part, based upon the detection of PVCs. For example, DVO may be controlled to provide for increasingly aggressive DVO pacing with increasingly higher PVC densities. In a third mode, shown in step 1310, the pacer again remains in DDD mode while DVO is performed in accordance with the standard DVO techniques described herein. However, DAO is also activated and operates in accordance with an alternative DAO technique wherein the DAO rate is controlled, at least in part, based upon the detection of intrinsic ventricular events. For example, the DAO rate may be increased whenever the DVO rate is increased as a result of detection of breakthrough R-waves. By implementing DVO in accordance with the various modes of steps 1306-1310, the aforementioned PMT problems associated with implementing DVO in the DDD pacing mode are substantially avoided.

5. VVI Pacer with Heart Rate Stability Detector

Figure 13:
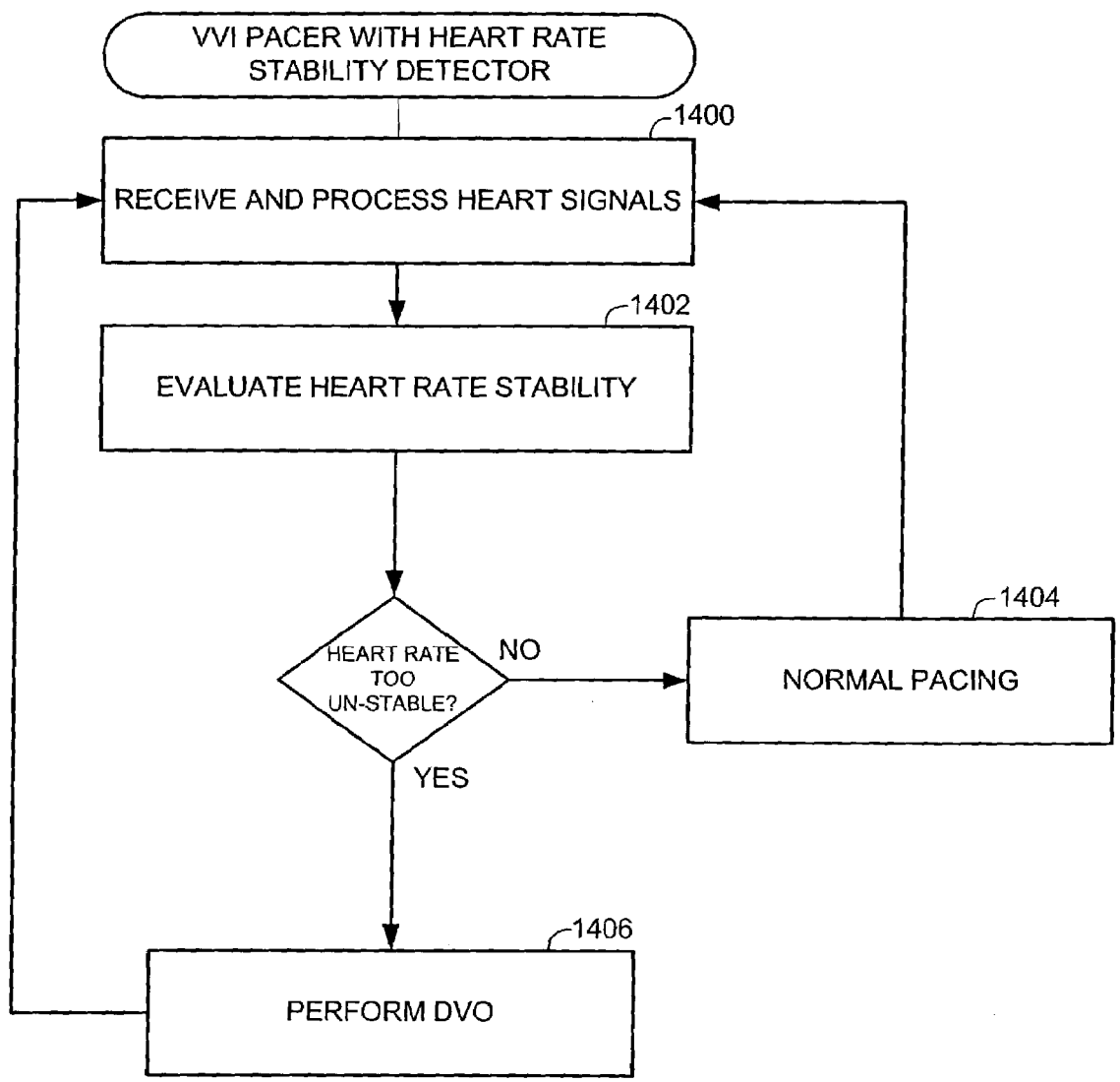
FIG. 13 is a flow chart providing an overview of the fourth DVO method wherein the stimulation device of FIGS. 1 and 2 operates in a VVI mode with a heart rate stability detector enabled.

FIG. 13 illustrates a method for activating and deactivating DVO within a VVI pacer provided with a heart rate stability detector for determining the amount of variation within the heart rate at any given time (such as heart rate stability detector 128 of FIG. 2). At step 1400, the microcontroller of the implantable device receives and process electrical signals from the heart and, at step 1402, employs the heart rate stability detector to determine the stability in the heart rate and compare it against a preprogrammed threshold. Preferably, the heart rate stability detector detects the stability of the ventricular rate. However, in other implementations, heart rate stability may be detected based on the atrial rate or on a combination atrial and ventricular rates. As with the PVC threshold described above, the heart rate stability threshold may be programmed by the physician using the external programmer or may be preset within the device based on values obtained from routine studies identifying optimal heart rate stability values at which to activate DVO. A suitable ventricular heart rate stability threshold value is in the range of 50-100 ms. Rate stability detection and related techniques, such as interval stability, are described in U.S. Pat. Nos. 5,941,831 and 4,830,006, which are incorporated herein by reference.

While the heart rate is reasonably stable, DVO remains inactive and normal pacing is performed, at step 1404, since DVO rate smoothing is not required while the hear rate is already stable. However, if the heart rate becomes too unstable, DVO is activated, at step 1406. DVO is activate while the heart rate is unstable to perform rate smoothing in an effort to reduce the risk of onset of AF or other arrhythmias.

6. VVI Pacer with PVC Density Detector

Figure 14:
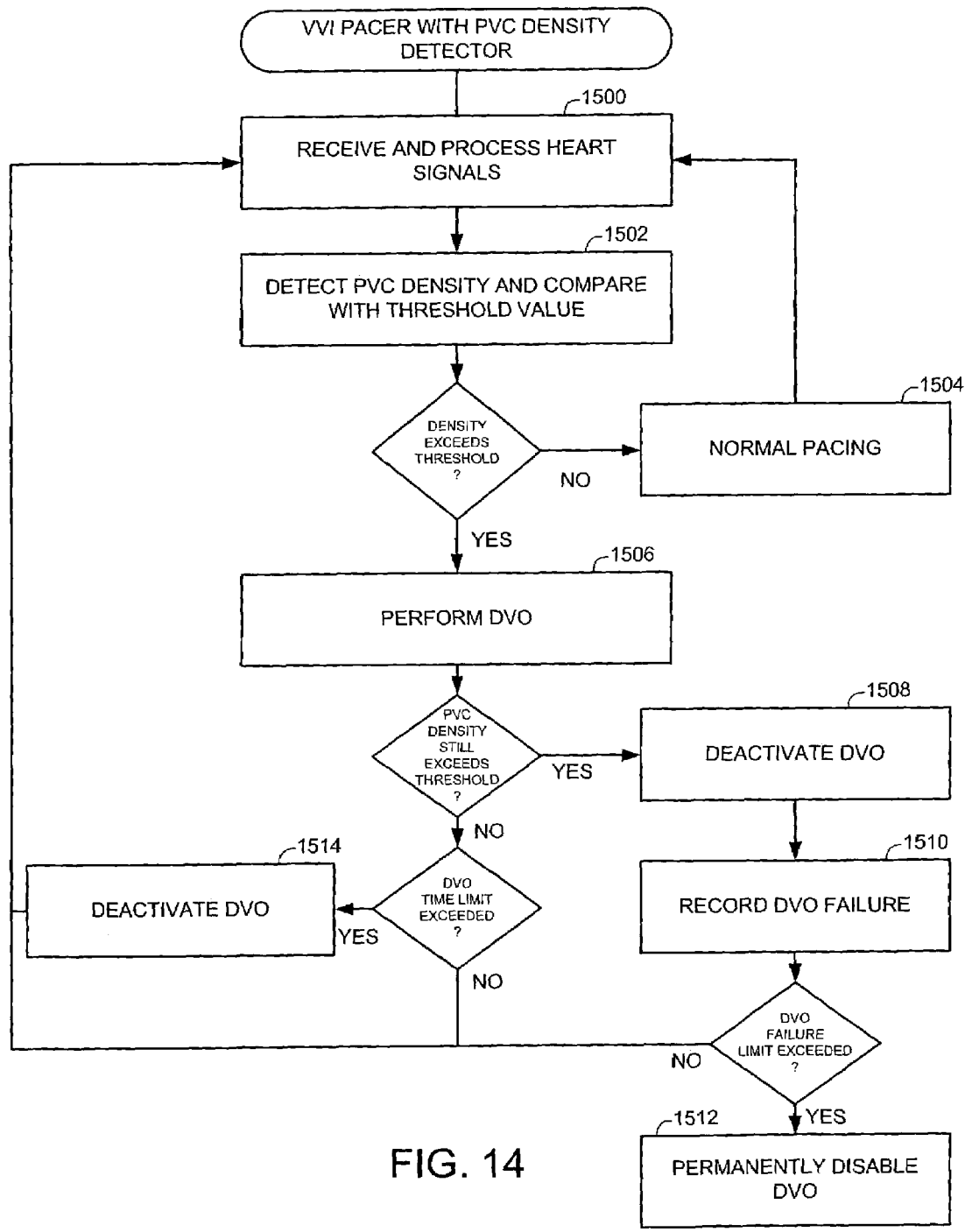
FIG. 14 is a flow chart providing an overview of the fifth DVO method wherein the stimulation device of FIGS. 1 and 2 operates in a VVI mode with a PVC density detector enabled.

FIG. 14 illustrates a method for activating and deactivating DVO within a VVI pacer provided with a PVC density detector for determining the density of PVCs. Note that the PVC density detector for use with the VVI pacer differs from the PVC density detector described above for use with the DDD pacer. Within a VVI pacer, P-waves are not detected and A-pulses are not generated, hence PVCs cannot be detected merely by determining whether an R-wave occurs prior to an expected A-pulse or P-wave. Rather, the density of the PVCs is detected as follows. In one example, R-R intervals are continuously tracked and a running average of the R-R intervals is calculated. Individual R-R intervals are compared against the running average and any R-R interval that is considerably shorter than the running average is deemed to be a PVC and the PVC density is derived therefrom. Routine statistical techniques are employed to determine the statistical variance with the patient's R-R intervals so that PVCs can reliably be detected. In one specific example, any R-R interval that is more than one standard deviation less than the current average R-R interval is deemed to be a PVC. Other possible techniques may be employed to evaluate the density of PVCs using VVI pacers. Note that reliable detection of individual PVCs is not required, rather only an evaluation of the density of PVCs is required, which need only be a suitable approximation of the true the density of PVCs.

At step 1500, the microcontroller receives and process electrical signals from the heart and, at step 1502, employs the PVC density detector to determine the PVC density and compare it against a predetermined threshold value. As above, the threshold value may be preprogrammed by the physician or preset within the device. The same exemplary PVC density threshold value of as set forth above may be used. While the density of PVCs remains below the threshold, DVO remains inactive and normal pacing is performed, at step 1504, since, as noted above, DVO rate smoothing is not required while the density of PVCs is low. However, if the density of PVCs exceeds the threshold, DVO is activated, at step 1506. DVO is activated while the PVC density is high in an effort to smooth the ventricular rate so as to decrease the occurrences of PVCs.

Unlike the method described above in connection with FIG. 12 for use with a DDI pacer, the method of FIG. 14 is for use with a VVI pacer, which cannot be switched to a safe DDI mode. Hence, care must be taken to ensure that DVO does not inadvertently trigger an increase the number of PVCs, potentially trigger a serious arrhythmia, such as VF. Accordingly, the PVC density after DVO is activated is monitored and, if it still exceeds the threshold after a predetermined period of time which may be, for example, thirty seconds, DVO is deactivated at step 1508. Diagnostic information is stored at step 1510 to indicate the failure of DVO to reduce PVCs. Assuming the number of DVO failures does not exceed a predetermined DVO failure threshold, processing continues at step 1500, possibility resulting in additional DVO failures. Once the number of DVO failures exceeds the DVO failure threshold, DVO is completely deactivated for the patient at step 1512. A suitable threshold for the number of DVO failures triggering complete deactivation of the DVO is 3. Once completely deactivated, DVO can only be re-enabled by the physician via re-programming of the implantable device. In this manner, the DVO is prevented from being repeatedly activated even though it has been found to be ineffective in reducing the density of PVCs.

Note also that whenever DVO is activated at step 1506, a timer is also activated. DVO is only performed for a predetermined amount of time following activation, such as for 30 minutes. Once the time limit has expired, DVO is again deactivated at step 1514. Deactivation following expiration of the timer is not recorded as a DVO failure and does not count toward determining whether to completely deactivate DVO.

Techniques described with respect to FIG. 14 for deactivating DVO, if PVC densities increase, can also be applied in connection with the techniques of FIG. 13, if heart rate stability significantly decreases following activation of DVO.

7. VVI Pacer for use with Patient with Chronic AF

Figure 15:
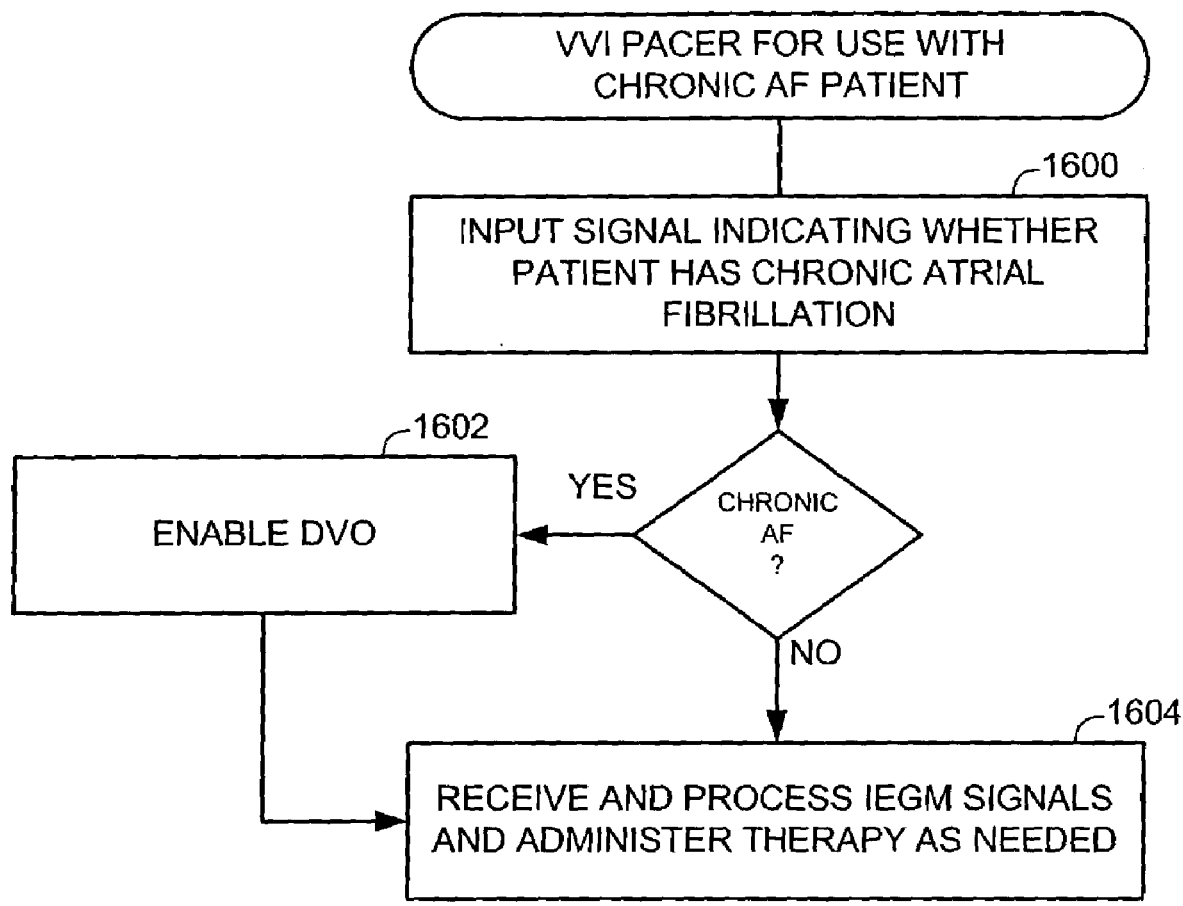
FIG. 15 is a flow chart providing an overview of the sixth DVO method wherein the stimulation device of FIGS. 1 and 2 operates in a VVI mode for use with a patient having chronic AF.

FIG. 15 illustrates a method for use with a VVI pacer provided without either a heart rate stability detector or PVC density detector. At step 1600, a programming signal is received from the external programmer indicating whether the patient has chronic AF. If the patient has chronic AF, DVO is performed constantly; otherwise not at all. The programs signal is generated by the external programmer under the supervision and control of the physician. If the patient has chronic AF as indicated by the input signal (received via telemetry circuit 100 of FIG. 2), DVO is activated at step 1602 and remains active continuously (or at least until another programming signal is received from the external programmer indicating that the patient no longer has chronic AF). If the patient does not have chronic AF, DVO is not activated at all. Rather, at step 1604, the pacer performs normal pacing therapy.

8. Adaptive Techniques

With reference to FIGS. 16 and 17, adaptive dynamic ventricular overdrive pacing techniques will now be described. The adaptive ventricular overdrive techniques of may exploit substantially the same logic employed in connection with the adaptive atrial overdrive pacing techniques of FIGS. 6-8. Accordingly, the general logic of the adaptive techniques will not be described again in detail. Rather the adaptive techniques will only be summarized with respect to ventricular overdrive pacing, with pertinent differences described in greater detail. First, as shown in FIG. 16, an adaptive technique for automatically adjusting overdrive pacing parameters so as to achieve a target degree of smoothness within the ventricular rate is provided. At steps 1700 and 1701, the implantable device receives a set of initial ventricular overdrive pacing control parameters along with a target degree of smoothness. Depending upon the particular ventricular overdrive pacing technique, the programmable values may be representative of: a ventricular overdrive pacing rate; a ventricular overdrive pacing margin; a ventricular pacing cycle length; a number of ventricular pacing pulses prior to pacing cycle length extension ($Z_{VENT.}$); an amount of time prior to a ventricular pacing cycle length extension; a number of un-paced ventricular pulses prior to pacing cycle length extension; a magnitude of ventricular rate increments ($Y_{VENT}$); a magnitude of ventricular rate decrement ($W_{VENT}$); a ventricular search window duration ($X_{VENT}$); a pacemaker base rate; and a sensor modulated base rate. The initial set of ventricular overdrive control parameters and the target degree of smoothness are both specified by the physician, using an external programmer. The values are transmitted to the implanted device, then stored in memory for subsequent use during episodes of ventricular overdrive pacing.

The target degree of smoothness is a numerical value representative of the optimal degree of smoothness that the implantable device will seek to achieve, and may be represented by a target range of smoothness values. The degree of smoothness in the ventricular rate may be represented, for example, as a degree of randomness in the ventricular rate, which in turn may be represented as one or more of: a degree of entropy in the ventricular rate; a chaos dimensionality associated with the ventricular rate (based on, for example, a scaling exponent); a spectral coefficient associated with the ventricular rate; or a mean and standard deviation in the ventricular rate. Techniques for representing the degree of randomness in the heart rate of a patient are described in U.S. patent application Ser. No., 10/017,836 entitled "Dynamic Control Of Overdrive Pacing Based On Degree Of Randomness Within Heart Rate", of Mark Kroll, filed Dec. 12, 2001, which is incorporated herein by reference. Other techniques for representing the degree of smoothness within the ventricular rate may alternatively be employed and no attempt is made here in to list all possible techniques.

At step 1702, the ventricular overdrive unit overdrive paces the ventricles in accordance with the initial input set of control parameters. Then, at stepped 1704, then the degree of smoothness within the ventricular rate is evaluated by the ventricular overdrive unit. Techniques for evaluating a degree of smoothness within of the heart rate of a patient (when represented in terms of a degree of randomness) are also set forth in the above-referenced patent application. Also, at step 1704, the ventricular overdrive unit compares the degree of smoothness detected within the ventricular rate with the target degree of smoothness to determine, for example, if it lies within the target range. If so, then no adjustment to the ventricular overdrive pacing control parameters are performed. However, if the actual degree of smoothness does not lie within the target range, the ventricular overdrive pacing parameters are automatically adjusted in an attempt to achieve the target degree of smoothness.

As with the atrial technique described above, the specific adjustments to the ventricular overdrive control parameters depend upon the particular programmable value being adjusted. In some cases, the value may need to be increased so as to cause an increase in the degree of smoothness. In other cases, the value may need to be decreased so as to cause an increase in the degree of smoothness. The direction of the adjustment and the magnitude of the adjustment are set so as to achieve a negative feedback loop which converges the actual degree of smoothness to the target degree of smoothness. To this end, routine experiments are performed to determine optimal values for adjusting the various parameters to achieve the desired feedback loop and to eliminate adjustment values, if any, which may result in a positive feedback loop causing the actual degree of smoothness to deviate from the target degree of smoothness, rather than to converge to the target degree of smoothness. The resulting adjustment in the values may be linear or non-linear, depending upon the particular programmable values and depending upon the amount of difference, if any, between the actual degree of smoothness and the target degree of smoothness. As with the atrial technique, a wide range of possible adjustments can be employed depending upon the characteristics of the overdrive pacing technique being implemented. In some cases, two or more programmable values may be adjusted simultaneously.

Once adjustments have been made to the ventricular control parameters, processing returns to step 1702 where further overdrive pacing of the ventricles is performed in accordance with the adjusted set of control parameters. Again, at step 1704, the resulting in degree of smoothness is evaluated and compared with the target degree of smoothness, and further adjustments, if needed, are made at step 1706. While ventricular overdrive pacing is performed, steps 1702-1706 are performed sequentially to repeatedly adjust the ventricular overdrive control parameters, if needed, to maintain the target degree of smoothness. Hence, any changes in the characteristics of the ventricular heart rate of the patient, perhaps brought on by exercise, arrhythmias, or the like, are automatically compensated.

Note that the target degree of smoothness need not specify the smoothest possible ventricular rate. In many cases, the target degree of smoothness will be less than the smoothest possible ventricular rate that can be achieved. As noted above, the degree of smoothness in the ventricular rate can generally be increased by elevating the ventricular pacing rate, however such rate increases are not necessarily always desirable, particularly if the resulting ventricular rate would be abnormally high. Accordingly, the target degree of smoothness (or target range of smoothness values) is often set to a value less than the smoothest possible ventricular rate that could potentially be achieved. As noted above, the physician programs the target agreement smoothness using an external programmer based on the overall needs of the patient. The external programmer may be preprogrammed with default smoothness values, which the physician adjusts if desired. The default smoothness values may be determined in advance via routine experimentation based on populations of patients in which ventricular overdrive pacing has been activated. Also, it should be understood that the target degree of smoothness specified by the physician will not always be achievable via the adjustment of the control parameters. The adaptive technique works to achieve a degree of smoothness most closely approximating the target degree of smoothness.

Thus, FIG. 16 sets forth, at a high-level, an adaptive technique for automatically adjusting ventricular overdrive pacing control parameters so as to achieve a target degree of smoothness. FIG. 17 sets forth a similar technique for automatically adjusting the ventricular control parameters so as to achieve a target percentage of ventricular paced beats. The percentage-based technique is similar to the smoothness-based technique and will only be briefly summarized. At steps 1800 and 1801, the implantable device receives a set of initial ventricular overdrive pacing control parameters along with a target percentage of paced beats, initially specified by the physician. At steps 1802 and 1804, the ventricles are overdrive paced using the initial set of control parameters and the resulting percentage of paced beats vs. non-paced beats is evaluated and compared with the target percentage. Adjustments, if needed, are made to the ventricular overdrive pacing control parameters at step 1806 in an effort to achieve the target percentage of paced beats. As with the smoothness-based technique, the target percentage of paced beats will not always be achievable, but the device will periodically adjust the control parameters during ventricular overdrive pacing in an attempt to bring the actual percentage of pace beats as close to the target percentage as possible.

What have been described are various techniques for performing dynamic atrial or ventricular overdrive pacing. Although described primarily with reference to an example wherein the implanted device is an ICD, the above-described embodiments are applicable to other implanted cardiac stimulation devices as well, such as pacemakers without defibrillation capability. Also, although described primarily with respect to single site ventricular pacing, the techniques herein may be exploited within a multi-site pacing system. The various functional components of the exemplary systems may be implemented using any appropriate technology including, for example, microprocessors running software programs or application specific integrated circuits (ASICs) executing hard-wired logic operations. The exemplary embodiments described herein are merely illustrative and should not be construed as limiting the scope of the invention.

What is claimed is:

1. In an implantable cardiac stimulation device for implant within a patient wherein at least one pacing lead is implanted within the ventricles of the heart, a method comprising:
   pacing the ventricles at an overdrive pacing rate;
   monitoring for at least two intrinsic ventricular pulses within a predetermined period; and
   dynamically adjusting the ventricular overdrive pacing rate based on the detection of at least two intrinsic ventricular pulses within the predetermined period.

2. The method of claim 1 wherein pacing the ventricles at an overdrive pacing rate comprises:
   setting an initial ventricular overdrive pacing rate equal to a default rate.

3. The method of claim 1 wherein dynamically adjusting the overdrive pacing rate comprises:
   detecting intrinsic beats occurring during overdrive pacing; and
   if at least two intrinsic heart beats are detected within a first predetermined period of time, increasing the overdrive pacing rate by a predetermined rate increment, and
   if at least two intrinsic heart beats are not detected within a second predetermined period of time, decreasing the overdrive pacing rate by a predetermined rate decrement.

4. The method of claim 3 wherein the predetermined rate increment is in the range of 2 to 25 beats per minute (bpm) and the predetermined rate decrement is in the range of 1-5 bpm.

5. The method of claim 1 wherein dynamically adjusting the overdrive pacing rate comprises:
   detecting intrinsic beats occurring during overdrive pacing; and
   if at least two intrinsic heart beats are detected within a first predetermined number of overdrive beats, increasing the overdrive pacing rate by a predetermined rate increment, and
   if at least two intrinsic heart beats are not detected within a second predetermined number of overdrive beats, decreasing the overdrive pacing rate by a predetermined rate decrement.

6. The method of claim 1 further comprising determining whether to activate ventricular overdrive pacing.

7. The method of claim 6 wherein the stimulation device is configured to provide a tracking mode and a non-tracking mode and wherein determining whether to activate ventricular overdrive pacing comprises:
   detecting whether the stimulation device is in a tracking mode or a non-tracking mode; and
   performing ventricular overdrive pacing only while in the non-tracking mode.

8. The method of claim 6 wherein the stimulation device is a DDI device incorporating an atrial fibrillation detector and wherein determining whether to activate ventricular overdrive pacing comprises:
   detecting atrial fibrillation; and
   performing ventricular overdrive pacing only during atrial fibrillation.

9. The method of claim 6 wherein the stimulation device includes a premature ventricular contraction (PVC) density detector and wherein determining whether to activate ventricular overdrive pacing comprises:
   detecting a density of PVCs;
   comparing the density of PVCs with a predetermined threshold; and
   performing ventricular overdrive pacing only while the density exceeds the threshold.

10. The method of claim 9 wherein the stimulation device is capable of operating in a DDD mode and in a DDI mode and wherein performing ventricular overdrive pacing while the density exceeds the threshold comprises switching the device to the DDI mode whenever ventricular overdrive pacing is activated.

11. The method of claim 9 wherein the stimulation device is capable of operating in a DDD mode and wherein performing ventricular overdrive pacing while the density exceeds the threshold comprises controlling ventricular overdrive pacing based, in part, on the density of PVCs.

12. The method of claim 9 wherein the stimulation device is capable of operating in a DDD mode and capable of performing atrial overdrive pacing and wherein performing ventricular overdrive pacing while the density exceeds the threshold comprises activating atrial overdrive pacing.

13. The method of claim 6 wherein the stimulation device is a VVI device incorporating a heart rate stability detector and wherein determining whether to activate ventricular overdrive pacing comprises:
   detecting a degree of instability in the heart rate;
   comparing the degree of instability in the heart rate with a predetermined threshold; and
   performing ventricular overdrive pacing only while the degree of instability exceeds the threshold.

14. The method of claim 6 wherein the stimulation device is a VVI device incorporating a premature ventricular contraction (PVC) density detector and wherein determining whether to activate ventricular overdrive pacing comprises:
   detecting a density of PVCs;
   comparing the density of PVCs with a predetermined threshold; and
   activating ventricular overdrive pacing only if the density exceeds the threshold.

15. The method of claim 14 wherein the stimulation device includes a heart rate stability detector and wherein the method further comprises:
   comparing the density of PVCs occurring following activation of ventricular overdrive pacing with the predetermined threshold; and
   deactivating ventricular overdrive pacing if the density of PVCs still exceeds the threshold.

16. The method of claim 6 wherein the stimulation device is a VVI device and wherein determining whether to activate ventricular overdrive pacing comprises:

inputting a signal indicating whether the patient has chronic atrial fibrillation; and performing ventricular overdrive pacing at all times if the signal indicates the patient has chronic atrial fibrillation.

17. The method of claim 1 wherein the step of dynamically adjusting the overdrive pacing rate is controlled so as to smooth the ventricular heart rate.

18. The method of claim 17 wherein the characteristics of the overdrive pacing rate are specified by a set of control parameters and wherein dynamically adjusting the overdrive pacing rate comprises:

determining a degree of smoothness achieved during ventricular overdrive pacing; and adaptively varying the control parameters so as to achieve a target degree of smoothness.

19. The method of claim 1 wherein dynamically adjusting the overdrive pacing rate is controlled to maintain a selected percentage of ventricular paced beats.

20. The method of claim 19 wherein the characteristics of the overdrive pacing rate are specified by a set of control parameters and wherein dynamically adjusting the overdrive pacing rate comprises:

determining the percentage of overdrive paced beats achieved during ventricular overdrive pacing; and adaptively varying the control parameters so as to achieve a target percentage of overdrive paced beats.

21. In an implantable cardiac stimulation device for implant within a patient wherein at least one pacing lead is implanted within the ventricles of the heart, a pacing system comprising:

intrinsic pulse detection circuitry operative to detect intrinsic ventricular pulses;

pulse generation circuitry operative to generate overdrive pacing pulses for delivery to the ventricles at an overdrive pacing rate; and a ventricular overdrive pacing controller operative to dynamically adjust the ventricular overdrive pacing rate of the pulse generation circuitry based on detection of at least two intrinsic ventricular pulses within a predetermined period.

22. In an implantable cardiac stimulation device for implant within a patient wherein at least one pacing lead is implanted within the ventricles of the heart, a pacing system comprising:

means for generating overdrive pacing pulses for delivery to the ventricles at an overdrive pacing rate;

means for detecting at least two intrinsic ventricular pulses within a predetermined period; and means for dynamically adjust the ventricular overdrive pacing rate based on the detection of at least two intrinsic ventricular pulses within the predetermined period.

* * * * *